US007407939B2

(12) United States Patent
Livnah et al.

(10) Patent No.: US 7,407,939 B2
(45) Date of Patent: Aug. 5, 2008

(54) PROTEIN KINASE INHIBITORS COMPRISING ATP MIMETICS CONJUGATED TO PEPTIDES OR PEPTIDOMIMETICS

(75) Inventors: Nurit Livnah, Mazkeret Batya (IL); Tamar Yechezkel, Ramat-Gan (IL); Yosef Salitra, Rehovot (IL); Boris Perlmutter, Lod (IL); Onsat Ohne, Kfar Saba (IL); Ilana Cohen, Nes Ziona (IL); Pninit Litman, Nes Ziona (IL); Hanoch Senderowitz, Tel Aviv (IL)

(73) Assignee: CureGenics Ltd., Rehovot (IL)

( * ) Notice: Subject to any disclaimer, the term of this patent is extended or adjusted under 35 U.S.C. 154(b) by 464 days.

(21) Appl. No.: 10/764,288

(22) Filed: Jan. 23, 2004

(65) Prior Publication Data

US 2005/0026840 A1    Feb. 3, 2005

Related U.S. Application Data

(63) Continuation of application No. PCT/IL02/00618, filed on Jul. 25, 2002.

(30) Foreign Application Priority Data

Jul. 26, 2001 (IL) .................................. 144583

(51) Int. Cl.
*A61K 38/08* (2006.01)
*A61K 31/47* (2006.01)
(52) U.S. Cl. .................. 514/16; 514/277; 514/279; 514/281; 530/329; 546/139
(58) Field of Classification Search .................. None
See application file for complete search history.

(56) References Cited

U.S. PATENT DOCUMENTS

| 5,475,110 | A | 12/1995 | Hudkins et al. | 546/256 |
|---|---|---|---|---|
| 5,516,771 | A | 5/1996 | Dionne et al. | 514/211 |
| 5,591,855 | A | 1/1997 | Hudkins et al. | 546/256 |
| 5,594,090 | A | 1/1997 | Bender | 530/218 |
| 5,650,407 | A | 7/1997 | Mallamo et al. | 514/185 |
| 5,654,427 | A | 8/1997 | Dionne et al. | 540/545 |
| 5,985,877 | A | 11/1999 | Dionne et al. | 514/250 |
| 6,034,097 | A | 3/2000 | DiMaio et al. | 514/308 |
| 6,174,993 | B1 | 1/2001 | Ben-Sasson | |
| 6,528,486 | B1 | 3/2003 | Larsen et al. | |
| 6,559,139 | B1 | 5/2003 | Johnson et al. | 514/168 |
| 6,667,337 | B2 | 12/2003 | Wilson | 514/449 |
| 6,943,148 | B1 | 9/2005 | Ekwuribe et al. | |
| 6,949,565 | B2 | 9/2005 | Livnah et al. | |
| 7,034,026 | B2 | 4/2006 | Barnett et al. | |
| 7,037,891 | B2 | 5/2006 | Ben-Sasson | |
| 2002/0065221 | A1 | 5/2002 | Cohen et al. | |
| 2003/0224383 | A1 | 12/2003 | West et al. | 435/6 |
| 2005/0026840 | A1 | 2/2005 | Livnah et al. | |
| 2005/0053594 | A1 | 3/2005 | Russel | |
| 2005/0106152 | A1 | 5/2005 | Hikichi et al. | |
| 2006/0142178 | A1 | 6/2006 | Sutton | |
| 2007/0078092 | A1 | 4/2007 | Livnah et al. | 514/2 |

FOREIGN PATENT DOCUMENTS

| WO | WO 96/11933 | 4/1996 |
|---|---|---|
| WO | WO 97/22360 | 6/1997 |
| WO | WO 01/70770 A2 | 9/2001 |
| WO | WO 01/91754 A1 | 12/2001 |
| WO | WO 03/010281 A2 | 2/2003 |

OTHER PUBLICATIONS

Dario R. Alessi et al., "Molecular basis for the substrate specificity of protein kinase B; comparison with MAPKAP kinase-1 and p70 S6 kinase," FEBS Letters 399, pp. 333-338 (1996).
Yi Fang et al., "Focal adhesion kinase affects the sensitivity of human hepatocellular carcinoma cell line SMMC-7721 to tumor necrosis factor-α/cycloheximide-induced apoptosis by regulating protein kinase B levels," *Eur. J. Biochem*, vol. 268, pp. 4513-4519 (2001).
Hiroyoshi Hidaka et al, "Isoquinolinesulfonamides, Novel and Potent Inhibitors of Cyclic Nucleotide Dependent Protein Kinase and Protein Kinase C," *Biochemistry*, vol. 23, pp. 5036-5041 (1984).
Chandra C. Kumar et al., "Expression, purification, characterization and homology modeling of active Akt/PKB, a key enzyme involved in cell survival signaling," *Biochimica et Biophysica Acta*, vol. 1526, pp. 257-268 (2001).
Ai-xue Liu et al., "AKT2, a Member of the Protein Kinase B Family, Is Activated by Growth Factors, v-Ha-*ras*, and v-*src* through Phosphatidylinositol 3-Kinase in Hunan Ovarian Epithelial Cancer Cells," *Cancer Research*, vol. 58, pp. 2973-2977 (1998).
Mart Loog et al., "Adenosine-5'-Carboxylic Acid Peptidyl Derivatives as Inhibitors of Protein Kinases," *Bioorganic & Medicinal Chemistry Letters*, vol. 9, pp. 1447-1452 (1999).
Robert Martell et al., "Effects of Protein Kinase Inhibitors 1(5-Isoquinolinesulfonyl)-2-Methylpiperazine Dihydrochloride (H-7) and N-[2-Guanidinoethyl]-5-Isoquinolinesulfonamide Hydrochloride (HA1004) on Calcitriol-Induced Differentiation of HL-60 Cells," *Biochemical Pharmacology*, vol. 37, pp. 635-640 (1988).
Karleen Nicholson et al., "The protein kinase B/Akt signalling pathway in human malignancy," *Cellular Signalling*, vol. 14, pp. 381-395 (2002).

(Continued)

*Primary Examiner*—Anish Gupta
(74) *Attorney, Agent, or Firm*—John P. White; Cooper & Dunham LLP

(57) ABSTRACT

The present invention provides small molecules having high affinity to the ATP binding site of protein kinases, which are conjugated to apeptide or peptidomimetic moiety which mimics the substrate of PKB. The chimeric compounds according to the present invention preferably serve as PKB inhibitors with improved activity and selectivity. Novel ATP mimetic compounds, particularly isoquinoline derivatives, conjugated with peptides or peptidomimetics are useful as inhibitors of protein kinases for experimental, medical, and drug design purposes. Furthermore, pharmaceutical compositions comprising these protein kinase inhibitors, and methods of using such compositions for treatment and diagnosis of cancers, diabetes, cardiovascular pathologies, hemorrhagic shock, obesity, inflammatory diseases, diseases of the central nervous system, and autoimmune disease, are disclosed.

17 Claims, 3 Drawing Sheets

OTHER PUBLICATIONS

Masakatsu Nishikawa et al., "1-(5-Isoquinolinesulfonyl)-2-Methylpiperazine(H-7), A Potent Inhibitor of Protein Kinases, Inhibits the Differentiation of HL-60 Cells Induced by horbol Diester", Life Sciences, vol. 39, pp. 1101-1107 (1986).

Toshiyuki Obata et al., "Peptide and Protein Library Screening Defines Optimal Substrate Motifs for AKT/PKB*," The Journal of Biological Chemistry, vol. 275, No. 46, pp. 36108-36115 (2000).

Keykavous Parang et al., "Mechanism-based design of a protein kinase inhibitor," Nature Structure Biology, vol. 8, No. 1, pp. 37-41 (2001).

G. Perez-Tenorio et al., "Activation of AKT/PKB in breast cancer predicts a worse outcome among endocrine treated patients," British Journal of Cancer, vol. 86, pp. 540-545 (2002).

Ricouart et al., "Design of Potent Protein Kinase Inhibitors Using the Bisubstrate Approach," J. Med. Chem., vol. 34, pp. 73-78 (1991).

Baljinder Salh et al., "Dysregulation of Phosphatidylinositol 3-Kinase and Downstream Effectors in Human Breast Cancer," Int. J. Cancer, vol. 98, pp. 148-154 (2002).

Martin Schlitzer et al., "Design, Synthesis and Early Structure—Activity Relationship of Farnesyltransferase Inhibitors Which Mimic Both the Peptidic and the Prenylic Substrate," Biorganic & Medicinal Chemistry, vol. 8, pp. 1991-2006 (2000).

Shuho Semba et al., "The in Vitro and in Vivo Effects of 2-(4-Morpholinyl)-8-phenylchromone (LY294002), a Specific Inhibitor of Phosphatidylinositol 3'-Kinase, in Human Colon Cancer Cells," Clinical Cancer Research, vol. 8, pp. 1957-1963 (2002).

V. Waldmann et al., "Absence of mutations in the pleckstrin homology (PH) domain of protein kinase B (PKB/Akt) in malignant melanoma" Melanoma Research, vol. 12, pp. 45-50 (2002).

Michael J. Zinda et al., "AKT-1, 2, and -3 are Expressed in Both Normal and Tumor Tissues of the Lung, Breast, Prostate, and Colon," Clinical Cancer Research, vol. 7, pp. 2475-2479 (2001).

Jian-Yuan Zhou et al., "Novel Vitamin D Analogs That Modulate Leukemic Cell Growth and Differentiation With Little Effect on Either Intestinal Calcium Absorption or Bone Calcium Mobilization" Blood, vol. 74 No. 1 pp. 82-93, (1989).

Gilbert Chu, "Cellular Responses to Cisplatin—The Roles of DNA-Binding Proteins and DNA Repair" The Journal of Biological Chemistry, vol. 269, No. 2, pp. 787-790, (1994).

Kay W. Colston et al., "Possible Role for Vitamin D in Controlling Breast Cancer Cell Proliferation" The Lancet, pp. 188-191 (1989).

David A. Fuchs et al., "Cytologic Evidence That Taxol, an Antineoplastic Agent From Taxus brevifolia, Acts as a Mitotic Spindle Poison" Cancer Treatment Reports vol. 62, No. 8, pp. 1219-1222 (1978).

Hiroyoshi Hidaka, et al. "Isoquinolinesulfonamides, Novel and Potent Inhibitors of Cyclic Nucleotide Dependent Protein Kinase and Protein Kinase C", Biochemistry, vol. 23, pp. 5036-5041 (1984).

Michelle M. Hill, et al. "Inhibition Of Protein Kinase B/Akt: Implications For Cancer Therapy" Pharmacology & Therapeutics, vol. 93 pp. 243-251 (2002).

Jerry A. Howle et al. "CIS-Dichlorodiammineplatinum (II) Persistent And Selective Inhibition Of Deoxyribonucleic Acid Synthesis In Vivo" Biochemical Pharmacology, vol. 19, pp. 2757-2762 (1970).

Maria Lindgren et al. "Cell-Penetrating Peptides" TiPS, vol. 21, pp. 99-103 (2000).

Ai-xue Liu, et al. "AKT2, A Member Of The Protein Kinase B Family, Is Activated By Growth Factors, v. Ha-ras, And v-src Through Phosphatidylinositol 3-Kinase In Human Ovarian Epithelial Cancel Cells" Cancer Research, vol. 58, pp. 2973-2977 (1998).

Narima M. lopes, et al. "Cell Kill Kinetics And Cell Cycle Effects Of Taxol On Human And Hamster Ovarian Cell Lines", Cancer Chemotherapy Pharmacol., vol. 32, pp. 235-242 (1993).

James J. Manfredi, et al. "Taxol: An Antimitotic Agent With A New Mechanism Of Action", Pharmac. Ther., vol. 25, pp. 83-125 (1984).

Mariann C. McElwain, et al., "Antiproliferative Effects In Vitro and In Vivo of 1,25-Dihydroxyvitamin $D_3$ and a Vitamin $D_3$ Analog in a Squamous Cell Carcinoma Model System" Molecular and Cellular Differentiation 3 (1): pp. 31-50 (1995).

Sheryl L. Parker, et al. "Cancer Statistics, 1996" CA Cancer J. Clin; vol. 46, No. 1 pp. 5-27 (1996).

Omathanu Pillai et al., "Polymers In Drug Delivery", Next Generation Therapeutics. Curnet Opinion In Chemical Biology, pp. 447-451 (2001).

Baljinder Salh et al., "Dysregulation of Phosphatidylinositol 3-Kinase and Downstream Effectors in Human Breast Cancer" Int. J. Cancer, vol. 98, pp. 148-154 (2002).

B. Salles, et al. "CIS-Pt $(NH_3)_2Cl_2$ And Trans-Pt $(NH_3)_2Cl_2$ Inhibit DNA Synthesis In Cultured L1210 Leukemia Cells", Biochemical and Biophysical Research Communications, vol. 112, No. 2, pp. 555-563 (1983).

Peter B. Schiff et al. "Taxol Stabilizes Microtubules In Mouse Fibroblast Cells", vol. 77, No. 3, pp. 1561-1565 (1980).

Suzanne E. Sherman et al., "Structural Aspects Of Platinum Anticancer Drug Interactions With DNA" Chem. Rev., vol. 87, pp. 1153-1181 (1987).

Prati Pal Singh et al. "Immunomodulation by Morphine in Plasmodium Berghei-Infected Mice" Life Sciences, vol. 54, No. 5, pp. 331-339 (1994).

George P. Studzinski, et al. "Potentiation of 1-β-D-Arabinofuranosylcytosine Cytotoxicity to HL-60 Cells by 1,25-Dihydroxyvitamin D3 Correlates with Reduced Rate of Maturation of DNA Replication Intermediates" Cancer Research, vol. 51, pp. 3451-3455 (1991).

V. Waldmann, et al., "Absence Of Mutations In The Pleckstrin Homology (PH) Domain Of Protein Kinase B (PKB/Akt) In Malignant Melanoma" Melanoma Research, vol. 12, pp. 45-50 (2002).

Yongde Liao et al., "Increase Of AKT/PKB Expression Correlates with Gleason Pattern in Human Prostate Cancer" Int. J. Cancer, vol. 107, pp. 676-680 (2003).

A. Belleli, et al. "A Protective Role Of 1,25-Dihydroxyvitamin D3, In Chemically Induced Rat Colon Carcinogenesis" Carcinogenesis, vol. 13, No. 12, pp. 2293-2298 (1992).

Jeffrey W. Clark et al., "Effects of analogs of 1,25(OH) 2 Vitamin D3 on the proliferation and differentiation of the human chronic myelogenous leukemia cell line, RWLeu-4", J. Cancer Res. Clin. Oncol., vol. 118, pp. 190-194 (1992).

Kawai et al., "Functional annotation of a full-length mouse cDNA collection," Nature (2001) 408: 685-690.

U.S. Appl. No. 11/862,542, filed Sep. 27, 2007, Livnah et al.

Reuveni et al., "Toward a PKB inhibitor: Modification of a selective PKA inhibitor by rational design", Biochemistry, 2002, 41:10304-10314.

Litman et al., "A novel substrate mimetic inhibitor of PKB/Akt inhibits prostate cancer tumor growth in mice by blocking the PKB pathway", Biochemistry, 2007, 46(16):4716-4724.

Cross et al., "Inhibition of glycogen synthase kinase-3 by insulin mediated by protein kinase B", Nature, 1995, 378:21-28, p785-789.

Niv et al., "Sequence-based design of kinase inhibitors applicable for therapeutics and target identification", Journal of Biological Chemistry, 2004, 279(2):1242-1255.

Franke et al., "The protein kinase encoded by the AKT proto-oncogene is a target of the PDGF-activated phosphatidylinositol 3-kinase", Cell, 1995, 81:727-736.

The file history of U.S. Pat. No. 6,949,565.

The file history of U.S. Pat. No.2005/0026840.

US 7,407,939 B2

PROTEIN KINASE INHIBITORS COMPRISING ATP MIMETICS CONJUGATED TO PEPTIDES OR PEPTIDOMIMETICS

CROSS-REFERENCE TO RELATED APPLICATIONS

This application is a continuation of International application PCT/IL02/00618 filed Jul. 25, 2002, the entire content of which is expressly incorporated herein by reference thereto.

FIELD OF THE INVENTION

The present invention relates to ATP mimetics, particularly isoquinoline derivatives, conjugated to a peptide or peptidomimetic, pharmaceutical compositions containing the isoquinoline derivatives and conjugates, their use as inhibitors of protein kinase, as well as to processes for the preparation and use of such molecules.

BACKGROUND OF THE INVENTION

Protein kinases are involved in signal transduction pathways linking growth factors, hormones and other cell regulation molecules to cell growth, survival and metabolism under both normal and pathological conditions. The superfamily of protein kinases includes protein kinase A and protein kinase C, as well as the more recently discovered protein kinase B (PKB).

PKB is a newly recognized anti-apoptotic protein kinase whose activity is strongly elevated in human malignancies. PKB was originally discovered as a viral oncogene v-Akt in rat T-cell leukemia. It was later established that v-Akt is the oncogenic version of a cellular enzyme PKB/c-Akt, in which a truncated viral group specific antigen, gag, is fused in frame to the full length Akt-1 and is membrane bound whereas PKB/c-Akt is cytoplasmic. Sequencing of Akt revealed a high degree of homology to PKA (~75%) and PKC isozymes (~50%), a fact which led to its renaming as PKB.

PKB activation involves phosphorylation of two amino acid residues, Ser473 and Thr308. The enzyme is activated by the second messenger PIP3 produced by PI'-3-kinase. PIP3 binds to the pleckstrin homology (PH) domains of PKB, recruits it to the membrane where it is phosphorylated and converted to its activated form. Since PKB activation is PI'-3-kinase dependent, the persistent activation of certain protein tyrosine kinases, such as IGF-1 receptor, EGF receptor, PDGF receptor, pp60c-Src, and the like, leads to the persistent activation of PKB which is indeed encountered in many tumors. Deletions in the gene coding for the tumor suppressor PTEN also induce the persistent activation of PKB/cAkt since it is the negative regulator of this enzyme. Also, PKB is overexpressed in 15% of ovarian cancers, 12% of pancreatic cancers and 3% of breast cancers, and was shown to produce a survival signal that protects cells from apoptosis thus contributing to resistance to chemotherapy.

PKB has emerged as a crucial regulator of widely divergent cellular processes including apoptosis, proliferation, differentiation and metabolism. Disruption of normal PKB/Akt signaling has now been documented as a frequent occurrence in several human cancers and the enzyme appears to play an important role in their progression (Nicholson and Anderson, Cellular Signalling 14, 381, 2002). Therefore PKB is, in principle, an attractive drug target for the treatment of cancer. Ideally, a drug that inhibits PKB should cause both cell cycle arrest and promote appoptosis. Such activity would result in increased cell death of tumor tissue where PKB is elevated, and in decreased resistance to chemoterapy agents.

These molecular properties of PKB and its central role in tumorigenesis, implies that this protein kinase may be an attractive target for novel anti-cancer agents. To date no specific inhibitors of PKB are known in the art, nor are any of the disclosed inhibitors of protein kinases A and C known to act on PKB.

Hidaka H. et al. (Biochemistry, 32, 5036, 1984) describe a class of isoquinolinesulfonamides having inhibitory activity towards cyclic nucleotide dependent protein kinases (PKA and PKG) and protein kinases C (PKC). The same class of compounds is claimed in EP 061673, which discloses said compounds as having cardiovascular activity. Additional derivatives of isoquinolinesulfonyl were disclosed by Hidaka in EP 109023, U.S. Pat. No. 4,456,757, U.S. Pat. No. 4,525,589, and U.S. Pat. No. 4,560,755.

Antitumor activity has been suggested for some of these isoquinolinesulfonamides. Martell R. E. et al. (Biochem. Pharm., 37, 635, 1988) found effects of two isoquinolinesulfonamides, namely 1-(5-isoquinolinsulfonyl)-2-methylpiperazine (H-7) and N-[2-guanidinoethyl]-5-isoquinolinesulfonamide (HA-1004), which have a certain selectivity for PKC and cyclic nucleotide dependent protein kinases, respectively, on calcitriol-induced cell differentiation. Further, Nishikawa M. et al., Life Sci., 39, 1101, 1986), demonstrate that the same compound H-7 inhibits cell differentiation induced by phorbol diester.

International PCT application WO 93/13072 discloses 5-isoquinolinesulfonamide derivatives as protein kinase inhibiting agents wherein the claimed compounds all contain two sulfonyl moieties.

Other classes of compounds known in the prior art (EP-A-397060, DE-A-3914764 and EP-A-384349) showed the capacity of inhibiting protein kinases, however, said compounds have a chemical structure which is totally different from that of the compounds of the present invention. In addition, international PCT application WO 98/53050 discloses short peptides derived from the HJ loop of a serine/threonine kinase which modulate the activity of serine/threonine kinases.

The minimal consensus sequence for efficient phosphorylation by PIM was found by Alessi et al. (Fed. Eur. Biochem Soc., 399, 333, 1996). This is a 7-mer motif faith the most active peptide substrate having the sequence Arg-Pro-Arg-Thr-Ser-Ser-Phe (SEQ ID NO: 1). International application WO 97122360 discloses certain PKB substrate peptides having 7-amino acids length, useful as substrate for measuring PKB activity.

Obata et al. (J. Biol. Chem., 17, 36108, 2000) described the use of an oriented peptide library approach to determine optimal amino acid sequence of the PKB substrate. All the substrates identified contained the known motif having the sequence Arg-Xaa-Arg-Xaa-Xaa-Ser/Thr (SEQ ID NO: 2).

Ricouart et al. (J. Med. Chem. 1991, 34, 73-78), described conjugates of isoquinolinesulfonamides and peptides for the inhibition of PKA. Loog et al. (Bioorganic and Medicinal Chemistry Letters 1999, 9, 1447-1452), described a chimera with adenosine and peptides for the inhibition of PKA and PKC. The inhibition obtained with the disclosed compound is very poor. Schlitzer et al. (Bioorganic and Medicinal Chemistry, 2000, 1991-2006) deal with a small molecule linked to non-peptidic long chain moieties that are supposed to replace the peptide part of the substrate. The disclosed compounds show poor inhibitory activity.

Parang et al. (Nature Structural Biology 8, 37, 2001), describe peptide-ATP bisubstrate analogs of a protein kinase A inhibitor, wherein ATP is linked to a protein kinase peptide substrate. Nevertheless, this approach has a limitation of suboptimal pharmacokinetic properties. WO 01/70770 discloses bisubstrate inhibitors for the insulin receptor tyrosine kinase and a specific potent and selective inhibitor comprising an ATP-gamma-S linked to a peptide substrate analog via a two-carbon spacer.

Numerous disclosures in the background art and in co-pending International Patent Application WO 01/91754 by one of the present inventors relate to specific isoquinoline derivatives, which are PKB inhibitors. The present invention is directed to novel isoquinoline derivatives and more specifically isoquinoline conjugates, and excludes all known compounds previously claimed for their capacity to inhibit PKB.

The present invention overcomes the limitations of known inhibitors by providing ATP surrogates and peptidomimetics with protein target specificity.

SUMMARY OF THE INVENTION

It is an object of the present invention to provide specific inhibitors of protein kinases for medical, therapeutic and drug design purposes. It is yet another object of the present invention to provide such molecules, which are selective inhibitors of protein kinase B.

One aspect of the present invention involves the preparation of novel compounds which inhibit the activity of protein kinases. It has now been found that certain novel derivatives of isoquinolinesulfonamides, which are protein kinase inhibiting agents, when conjugated to a peptide or peptidomimetic, unexpectedly proved to be active towards a specific type of protein kinase, namely protein kinase B.

The present invention provides small molecules having high affinity to the ATP binding site of PKB, which are conjugated to a peptide or peptidomimetic moiety which mimics the substrate of PKB. These compounds are referred to herein as "chimeric" compounds. The chimeric compounds according to the present invention preferably serve as PKB inhibitors with improved activity and selectivity.

Another aspect of the present invention is directed to pharmaceutical compositions comprising as an active ingredient novel inhibitors of protein kinase and to methods for the preparation and use of pharmaceutical compositions comprising these novel inhibitors of protein kinases.

Another aspect of the present invention is directed to the use of pharmaceutical compositions comprising these protein kinase inhibitors for production of medicaments useful for the treatment or diagnosis of diseases and disorders. The present invention discloses methods of treatment of disorders involving protein kinase, including but not limited to cancers, cardiovascular pathologies, hemorrhagic shock, obesity, inflammatory diseases, diseases of the central nervous system, and autoimmune diseases.

The present invention further provides methods for modulating the activity of protein kinases in a subject, comprising administering a therapeutically effective amount of a protein kinase inhibitor.

Further aspects of the present invention are directed to methods for the diagnosis of diseases including in-vitro diagnosis using the compounds of the present invention, and in-vivo diagnosis comprising administering a pharmaceutical composition comprising a diagnostically useful amount of a protein kinase inhibitor prepared according to the principles of the present invention.

It is yet another object of the present invention to provide protein kinase inhibitors comprising peptidomimetic compounds having improved stability and cell permeability properties. Non limiting examples of such compounds include N-alkylation of selected peptide residues, side-chain modifications of selected peptide residues, non-natural amino acids, use of carbamate, urea, sulfonamide and hydrazine for peptide bond replacement, and incorporation of non-peptide moieties including but not limited to piperidine, piperazine and pyrrolidine, through a peptide or non-peptide bond. These peptidomimetic compounds may be used according to the present invention as the peptide substrate part of chimeric compounds. In addition these peptidomimetic compounds may be used as protein kinase inhibitors per se.

Preferred embodiments according to the present invention comprise a chimeric compound comprising both an ATP mimetic moiety and a peptidic substrate mimetic moiety connected by a spacer.

The ATP mimetic core includes but is not limited to dansyls, isoquinolines, quinolines and naphthalenes. The spacer is of varied lengths and conformations of any suitable chemistry including but not limited to amine, amide, thioether, oxyether, sulfonamide bond and the like. Non limiting examples for such spacers include sulfone amide derivatives, amino thiol derivatives and amino alcohol derivatives. The peptidic moiety comprises peptides or peptidomimetics. Such inhibitory peptides are designed based on any peptide which may serve as a PKB substrate.

More preferred embodiments of the present invention comprise a compound of Formula I

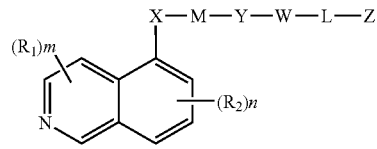

Formula I wherein:

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol nitro, cyano, or amino group;

m and n are each independently 0-3;

X is selected from the group consisting of $SO_2$—NH, S and O;

M represents substituted or unsubstituted alkylene of 1-4 carbon atoms;

Y is selected from the group consisting of amide, amine, urea, carbamate, hydrazine or sulfonamide;

W is absent or is selected form the group consisting of substituted or unsubstituted alkylene, aliphatic, aromatic or heterocyclic moiety, of 1-18 carbon atoms;

L is absent or is selected from the group consisting of amide, amine, urea, carbamate, hydrazine or sulfonamide; and Z is a peptide or peptidomimetic moiety of 4-12 residues in length capable of binding to the substrate site of PKB.

Preferably, $R_1$ and $R_2$ are independently selected from the group consisting of methyl, ethyl, ethoxy and dimethylamine;

m and n are each 1;

X is selected from the group consisting of $SO_2$—NH and S;

M represents substituted or unsubstituted alkylene of 2 carbon atoms;

Y is selected from the group consisting of amide and amine;

W is absent or is selected form the group consisting of substituted or unsubstituted alkylene, aliphatic, aromatic or heterocyclic moiety, of 1-5 carbon atoms;

L is absent or is selected from the group consisting of amide and amine; and

Z is a peptide or peptidomimetic moiety of 6-10 residues in length capable of binding to the substrate site of PKB.

According to certain currently more preferred embodiments the peptide substrate mimetic designated as Z in Formula I, comprises a sequence of seven residues that are referred to herein as $AA_1$ through $AA_7$. Each AA is selected from the group consisting of an amino acid, an amino acid analog, or an aliphatic, aromatic or, heterocyclic moiety, incorporated into the sequence to create a peptidomimetic moiety with improved pharmacological properties.

$AA_1$ and $AA_3$ are independently selected from the group consisting of: arginine or arginine analog; lysine or lysine analog; ornithine or ornithine analog; or an aliphatic, aromatic, or heterocyclic moiety bearing a group positively charged at physiological pH, such as an amine, guanidine or amidine, homoarginine, argininol.

$AA_2$ is selected from the group consisting of proline, proline analog or an aliphatic, aromatic or heterocyclic moiety, hydroxyproline, nipecotic acid, alanine, aminobutyric acid.

$AA_4$, $AA_5$, $AA_6$ are each independently selected from the group consisting of: diaminopropionic acid, diaminobutyric acid, ornithine, GlyNH2, Tyr or Tyr analog, Thr or Thr analog; Ser or Ser analog; Ala or Ala analog, Glu or Glu analog, Gly or Gly analog; an aliphatic, aromatic or heterocyclic residue bearing alky, benzyl, hydroxy, phenoxy alkoxy, sulfone, sulfoxide, phosphonate, phosphonate ester, amide or carbamoyl functionality, amino butyric acid, citrulline, serinol, phosphotyrosine and phosphotyrosine dimethyl ester.

$AA_7$ is selected from the group consisting of: Phe or Phe analog, Trp or an analog, Tyr or an analog, Leu or an analog, homoleucine or an analog, lie or an analog; aromatic moiety esters or aromatic substitutions of an amino acid; an aromatic, heterocyclic or branched aliphatic moiety, homophenylalanine, homoleucine, glutamic benzyl ester, naphtylalanine.

Due to the peptidomimetic nature of the preferred embodiments according to the invention, the bonds between AAs may be selected from the group consisting of: an amide, urea, carbamate, hydrate or sulfonamide bond. In the currently more preferred embodiments the bonds between the AAs are all amide bonds unless explicitly stated otherwise.

Additional preferred embodiments of the present invention comprise a compound of Formulae IIa-IId:

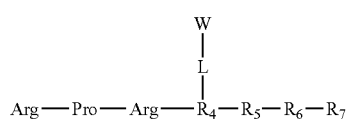

Formula IIa

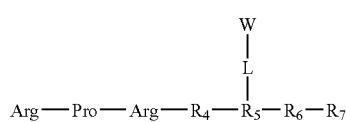

Formula IIb

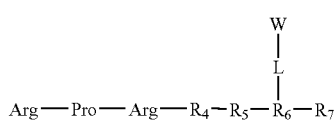

Formula IIc

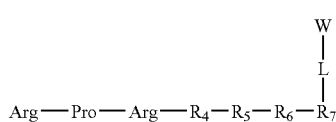

Formula IId wherein:

$R_4$, $R_5$, and $R_6$ are each independently selected from the group consisting of threonine, serine, glutamic acid allyl ester, homocitrulline, lysine, methionine, norleucine, omithine, arginine, glycine, diaminopropionic acid, diaminobutyric acid, GlyNH$_2$, and alanine; or are an $N^{\alpha}$-ω-functionalized derivative of an amino acid selected from the group of glycine, alanine and tyrosine;

$R_7$ is selected from the group consisting of phenylalanine, homoleucine, norleucine, glutamic acid allyl ester;

W is absent or is N-(8-sulfonamide-5-isoquinoline) ethylenediamine; and

L may be absent or is selected from the group consisting of glycine, (β-alanine, phenylalanine, aminobutyric acid and aminopentanoic acid.

Preferably, W is connected to $R_5$ as described in Formula IIb.

Currently most preferred embodiments of the present invention are the chimeric compounds of formulae III-VII:

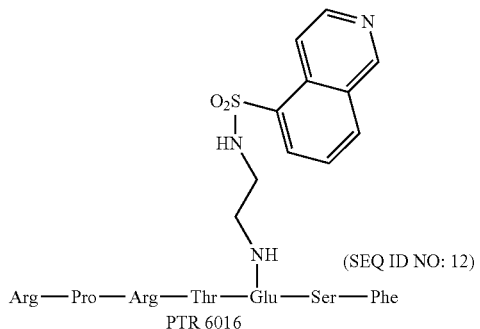

Formula III (SEQ ID NO: 12)

PTR 6016

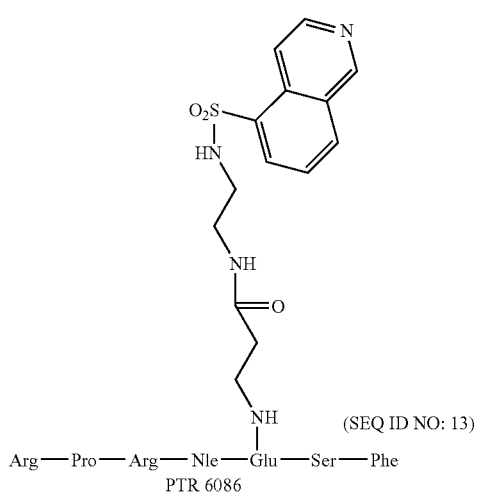

Formula IV (SEQ ID NO: 13)

PTR 6086

Formula V

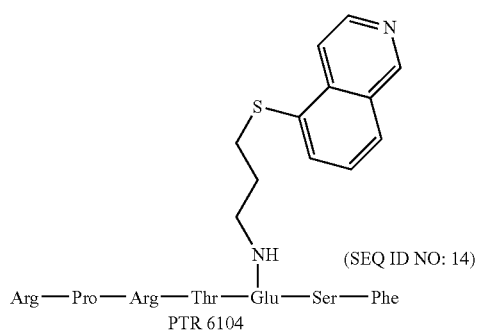

Arg—Pro—Arg—Thr—Glu—Ser—Phe (SEQ ID NO: 14)
PTR 6104

Formula VI

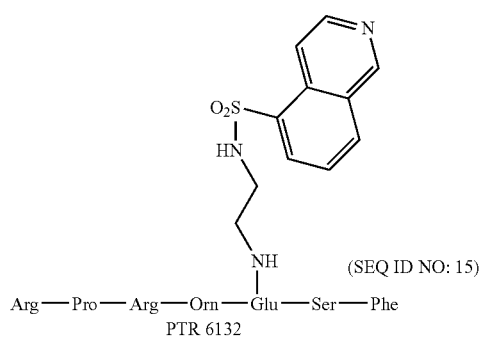

Arg—Pro—Arg—Orn—Glu—Ser—Phe (SEQ ID NO: 15)
PTR 6132

Formula VII

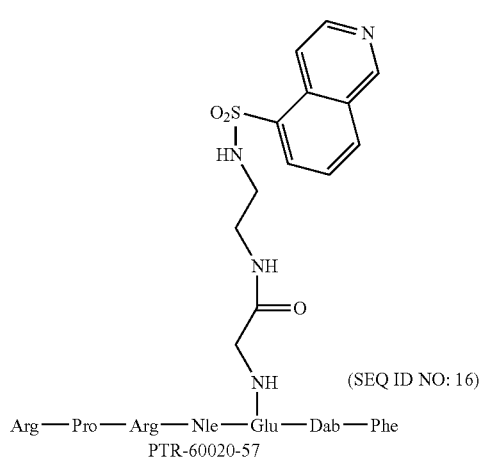

Arg—Pro—Arg—Nle—Glu—Dab—Phe (SEQ ID NO: 16)
PTR-60020-57

Currently most preferred are compounds having a sequence selected from:

Arg-Pro-Arg-Thr-Glu-(bAla-5-mercaptoaminopropyl-isoquinoline)-Ser-Phe (SEQ ID NO: 3).

Arg-Pro-Arg-Thr-Glu-(5-mercaptoaminopropyl-iso-quinoline)-Ser-Phe (SEQ ID NO: 4).

Arg-Pro-Arg-Orn-Glu-(5-aminoethylsulfonamide iso-quinoline)-Ser-Phe (SEQ ID NO: 5).

Arg-Pro-Arg-Nva-Glu-(5-mercaptoaminopropyl-iso-quinoline)-Ser-Phe (SEQ ID NO: 6).

Arg-Pro-Arg-Nle-Glu-(5-mercaptoaminopropyl-iso-quinoline)-Ser-Phe (SEQ ID NO: 7).

Arg-Pro-Arg-Orn-Glu-(Gly-5 -aminoethylsulfonamide)-Dab-Hol (SEQ ID NO: 8).

Arg-Pro-Arg-Nle-Glu-(Gly-5-aminoethylsulfonamide)-Dab-Phe (SEQ ID NO: 9).

Arg-Pro-Arg-Nle-Glu-(Gly-5-aminoethylsulfonamide)-Dab-Hol (SEQ ID NO: 10).

Essentially all of the uses known or envisioned in the prior art for protein kinase inhibitors, can be accomplished with the molecules of the present invention. These uses include therapy and diagnostic techniques.

By way of exemplification, the compounds disclosed in the present invention were selected for inhibition of Protein kinase B. Using the preparations and methods disclosed herein it is possible to obtain compounds that inhibit the activity of other types of protein kinases.

DETAILED DESCRIPTION OF THE INVENTION

Figure 1:
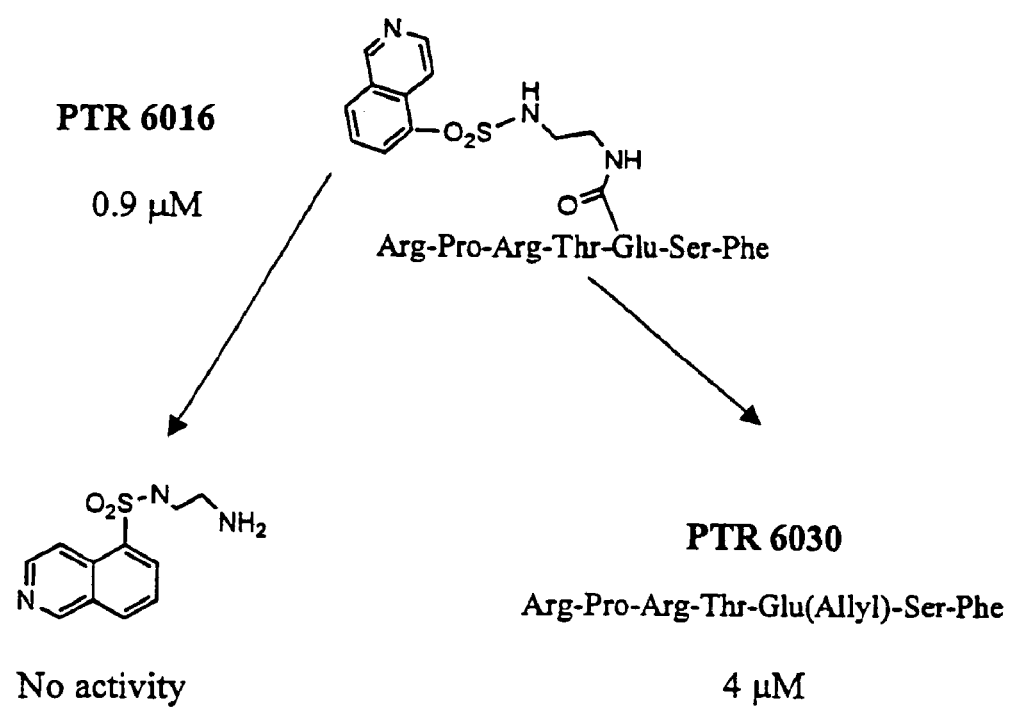
FIG. 1. The synergistic effect of chimeric compound PTR 6016 composed of an ATP mimic and a peptide substrate.

It is now disclosed that chimeric compounds according to the present invention are inhibitors of protein kinases. It is known that small molecules that share certain structural motifs may serve as "ATP mimetic" inhibitors. It has now been discovered that such moieties may be part of chimeric compounds comprising also a substrate mimetic moiety, which are potent inhibitors of protein kinases, particularly PKB, according to the present invention.

The disclosed protein kinase inhibitors are chimeric molecules which exhibit enhanced affinity toward certain protein kinase subtypes. In principle, the present invention provides for the first time highly active (in the nano molar range) inhibitors of protein kinase B. The preferred molecules generally have a molecular weight of less than about 1100 daltons. These and further advantages over the background art will become apparent from the description of the currently preferred embodiments of the present invention.

Preferred compounds according to the present invention are composed of small molecules having high affinity to the ATP binding site of PKB, which are conjugated to a peptide or peptido-mimetic moiety that mimics the substrate of PKB. The chimeric compounds according to the present invention preferably serve as PKB inhibitors with improved activity and selectivity.

The utility of the compositions according to the invention can be established by means of various assays as are well known in the art The preferred compounds of the present invention were found to be active in a panel of in-vitro assays, in inhibiting the activity of protein kinases and in induction of apoptosis in cancer cells.

Pharmaceutical compositions according to the present invention comprising pharmacologically active protein kinase inhibitors and a pharmaceutically acceptable carrier or diluent represent another embodiment of the invention, as do the methods for the treatment of a mammal in need thereof with a pharmaceutical composition comprising an effective amount of a protein kinase inhibitor according to the invention. Methods of treatment using the compositions of the invention are useful for therapy of cancers, diabetes, cardiovascular pathologies, hemorrhagic shock, obesity, inflammatory diseases, diseases of the central nervous system, and autoimmune diseases using such compositions.

The pharmaceutical compositions according to the present invention may be most preferably be used for prevention and treatment of malignancies selected from the group of Breast Cancer (Perez-Tenorio and Stal, Br.J.cancer 2002 86, 540-45, Salh et al, Int. J.cancer 2002 98,148-54); Ovarian cancer (Liu et al, cancer res. 1998 15, 2973-7); Prostate cancer (Zin et al, Clincancer.res. 2001 7,2475-9); Colon cancer (Semba at al, cilncancer.res. 2002 8,1957-63); Melanoma and skin cancer (Waldermnan, Wecker and Diechmann, Melanoma res. 2002 12, 45-50); Lung cancer (Zin et al, Clin.cancer.res. 2001 7,2475-9); and hepatocarcinoma (Fang et al, Eur. J. Biochem. 2001 268, 4513-9).

The pharmaceutical compositions according to the present invention advantageously comprise at least one protein kinase inhibitor. These pharmaceutical compositions may be administered by any suitable route of administration, including topically or systemically. Preferred modes of administration include but are not limited to parenteral routes such as intravenous and intramuscular injections, as well as via nasal or oral ingestion.

As is known to those skilled in the art the pharmaceutical compositions may be administered alone own or in conjunction with additional treatments for the conditions to be treated.

Terminology and Definitions

In the specification and in the claims the term "protein kinase" refers to a member of an enzyme superfamily which functions to phosphorylate one or more protein as described above.

As used herein and in the claims, the term "inhibitor" is interchangeably used to denote "antagonist" these terms define compositions which have the capability of decreasing certain enzyme activity or competing with the activity or function of a substrate of said enzyme.

As used herein and in the claims the term "chimeric compound" or "chimeric molecule" denotes an ATP mimic moiety conjugated to a PKB substrate mimetic part Examples for such chimeric compounds or conjugates are small molecules (and more specific isoquinoline derivatives) that mimic the ATP molecule of the PKB, conjugated to a peptide or a peptidomimetic moiety which is a PKB substrate mimetic. These molecules may preferably serve as PKB inhibitors with improved activity and selectivity.

As used herein "peptide" indicates a sequence of amino acids linked by peptide bonds. The peptide analogs of this invention comprise a sequence of 3 to 15 amino acid residues, preferably 4 to 12 residues, more preferably 5 to 10 amino acids, each residue being characterized by having an amino and a carboxy terminus.

The term "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "peptidomimetic" may be computer assisted.

The term "peptide analog" indicates molecule which has the amino acid sequence according to the invention except for one or more amino acid changes or one or more modification/replacement of an amide bond.

In the specification and in the claims the term "therapeutically effective amount" refers to the amount of protein kinase inhibitor or composition comprising same to administer to a host to achieve the desired results for the indications described herein, such as but not limited of cancers, diabetes, cardiovascular pathologies, hemorrhagic shock, obesity, inflammatory diseases, diseases of the central nervous system, and autoimmune diseases.

Certain abbreviations are used herein to describe this invention and the manner of making and using it For instance, ATP refers to adenosine three phosphate, BSA refers to bovine serum albumin, BTC refers to bis-(trichloromethyl) carbonate or triphosgene, DCM refers to dichloromethane, DIEA refers to diisopropyl-ethyl amine, DMF refers to dimethyl formamide, EDT refers to ethanedithiol, EDTA refers to ethylene diamine tetra acetate, ELISA refers to enzyme linked immuno sorbent assay, EGF refers to epithelial growth factor, FACS refers to fluorescence assisted cell sorter, HA refers to hemagglutinin HBTU refers to 1-hydroxybenztriazolyltetramethyl-uronium, HEPES refers to 4-(2-hydroxyethyl)-1-piperazineethanesulfonic acid, HOBT refers to 1-hydroxybenzotriazole, HRP refers to horse raddish peroxidase, IGF refers to insulin growth factor, MOPS refers to 4-morpholinepropanesulfonic acid, MPS refers to multiple parallel synthesis, NMP refers to N-methyl formamide, OPD refers to o-Phenylenediamine, PBS refers to phosphate buffer saline, PKA refers to protein kinase A, PKB refers to protein kinase B, PKC refers to protein kinase C, rpm refers to rounds per minute, SAR refers to structure-activity relationship, THF refers to tetrahydrofuran, TIS refers to tri-isopropyl-silane, TFA refers to trifluoric acetic acid.

The amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged.

List of non limiting examples of non-coded amino acids which where used in the present invention: Abu refers to 2-aminobutyric acid, Ape5 refers to aminopentanoic acid, ArgOl refers to argininol, bAla refers to β-Alanine, Bpa refers to 4-Benzoylphenylalanine, Bip refers to Beta-(4-biphenyl)-alanine, Dab refers to diaminobutyric acid, Dap refers to Diaminopropionic acid, Dim refers to Dimethoxyphenylalanine, Dpr refers to Diaminopropionic acid, Hol refers to homoleucine, HPhe refers to Homophenylalanine, Gaba refers to gamma aminobutyric acid. GlyNH2 refers to Aminoglycine, Nle refers to Norleucine, Nva refers to Norvaline, Orn refers to Ornithine, PheCarboxy refers to para carboxy Phenylalanine, PheCl refers to para chloro Phenylalanine, PheF refers to para fluoro Phenylalanine, PheMe refers to para methyl Phenylalanine, PheNH$_2$ refers to para amino Phenylalanine, PheNO$_2$ refers to para nitro Phenylalanine, Phg refers to Phenylglycine, Thi refers to Thienylalanine.

Pharmacology

The compounds of the present invention can be administered to a subject in a number of ways, which are well known in the art. Hereinafter, the term "subject" refers to the human or lower animal to whom compounds of the present invention are administered.

The novel pharmaceutical compositions of the present invention contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration.

Liquid forms may be prepared for oral administration or for injection, the term including subcutaneous, transdermal, intravenous, intrathecal, and other parenteral routes of administration. The liquid compositions include aqueous solutions, with or without organic cosolvents, aqueous or oil suspensions, emulsions with edible oils, as well as other micellar dispersions and similar pharmaceutical vehicles. In addition, the compositions of the present invention may be formed as aerosols, for intranasal and like administration. More preferred formulations include sustained release or depot formulations, which may provide a steady state pharmacokinetic profile.

However, it is evident to the man skilled in the art that dosages would be determined by the attending physician, according to the disease to be treated, method of administration, patient's age, weight, contraindications and the like.

All the compounds defined above are effective as inhibitors of protein kinase and can be used as active ingredients of pharmaceutical compositions for treatment of one, or simultaneously several, symptoms of the disorders defined above.

The compounds of the present invention are administered for the above-defined purposes in conventional pharmaceutical forms, with the required solvents diluents, excipients, etc. to produce a physiologically acceptable formulation. They can be administered by any of the conventional routes of administration.

It will be appreciated that the most appropriate administration of the pharmaceutical compositions of the present invention will depend on the type of disorder or disease being treated.

Chemistry:

Some of the preferred compounds of the present invention may conveniently be prepared using solution phase synthesis methods. Other methods known in the art to prepare isoquinoline compounds like those of the present invention, can be used and are comprised in the scope of the present invention. Preferred peptides according to the present invention may be synthesized using any method known in the art, including peptidomimetic methodologies. These methods include solid phase as well as solution phase synthesis methods. The conjugation of the peptidic and small molecule moieties may be performed using any methods known in the art, either by solid phase or solution phase chemistry. Non-limiting examples for these methods are described hereby.

By way of exemplification of the principles of the present invention, a search for inhibitory PKB chimeric compounds focused on SAR studies of certain molecules, as exemplified hereinbelow.

Preferred Embodiments

Protein kinases have more than one active site, they possess a catalytic site for ATP and a substrate-binding site. Preferred compounds according to the present invention can bind both sites at the same time and may have a synergistic effect that will give it unique potency and selectivity properties. These preferred compounds are chimeric molecules which are designed to include an ATP-mimetic molecule, connected via various spacers to a substrate-mimetic portion.

Preferred embodiments according to the present invention comprise a chimeric compound comprising both an ATP mimetic moiety and a peptidic substrate mimetic moiety connected by a spacer, as described in the following scheme I:

Scheme I

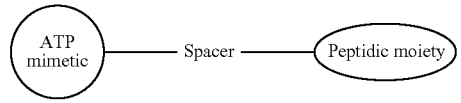

The ATP mimetic core includes but is not limited to dansyls, isoquinolines, quinolines and naphthalenes. The spacer is of varied lengths and conformations of any suitable chemistry including but not limited to amine, amide, thioether, oxyether, sulfonamide bond and the like. Non-limiting examples for such spacers include sulfone amide derivatives, amino thiol derivatives and amino alcohol derivatives. The peptidic moiety comprises peptides and peptidomimetics. Such inhibitory peptides may be designed based on any peptide which may serve as PKB substrate.

Additional more preferred embodiment of the present invention comprises a compound of Formula I:

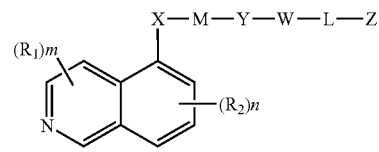

Formula I wherein:

$R_1$ and $R_2$ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group;

m and n are each independently 0-3;

X is selected from the group consisting of $SO_2$—NH, S and O;

M represents substituted or unsubstituted alkylene of 1-4 carbon atoms;

Y is selected from the group consisting of amide, amine, urea, carbamate, hydrazine or sulfonamide;

W is absent or is selected form the group consisting of substituted or unsubstituted alkylene, aliphatic, aromatic or heterocyclic moiety, of 1-18 carbon atoms;

L is absent or is selected from the group consisting of amide, amine, urea, carbamate, hydrazine or sulfonamide; and Z is a peptide or peptidomimetic moiety of 4-12 residues in length capable of binding to the substrate site of PKB.

Preferably, $R_1$ and $R_2$ are independently selected from the group consisting of methyl, ethyl ethoxy and dimethylamine;

m and n are each 1;

X is selected from the group consisting of $SO_2$—NH and S;

M represents substituted or unsubstituted alkylene of 2 carbon atoms;

Y is selected from the group consisting of amide and amine;

W is absent or is selected form the group consisting of substituted or unsubstituted alkylene, aliphatic, aromatic or heterocyclic moiety, of 1-5 carbon atoms;

L is absent or is selected from the group consisting of amide and amine; and

Z is a peptide or peptidomimetic moiety of 6-10 residues in length capable of binding to the substrate site of PKB.

Preferred peptide substrate and peptide substrate mimetics according to the present invention, forming part of the chimeric compounds are described in the following scheme:

$$AA_1-AA_2-AA_3-AA_4-AA_5-AA_6-AA_7$$

According to this scheme AA is selected from the group consisting of an amino acid, an amino acid analog, or an aliphatic, aromatic or heterocyclic moiety, incorporated into the sequence to create a peptidomimetic moiety with improved pharmacological properties.

$AA_1$ and $AA_3$ are independently selected from the group consisting of: arginine or arginine analog; lysine or lysine analog, ornithine or ornithine analog; or an aliphatic, aromatic, or heterocyclic moiety bearing a group positively charged at physiological pH, such as an amine, guanidine or amidine, homoarginine, argininol.

$AA_2$ is selected from the group consisting of proline, proline analog or an aliphatic, aromatic or heterocyclic moiety, hydroxyproline, nipecotic acid, alanine, aminobutyric acid.

$AA_4$, $AA_5$, $AA_6$ are independently selected from the group consisting of:

Diaminopropionic acid, diaminobutyric acid, Ornitine, GlyNH2, Tyr or Tyr analog, Thr or Thr analog; Ser or Ser analog, Ala or Ala analog, Glu or Glu analog, Gly or Gly analog; an aliphatic, aromatic or heterocyclic residue bearing alkyl, benzyl, hydroxy, phenoxy alkoxy, sulfone, sulfoxide, phosphonate, phosphonate ester, amide or carbamoyl functionality, amino butyric acid, citrulline, serinol, phosphotyrosine and phosphotyrosine dimethyl ester.

$AA_7$ is selected from the group consisting of: Phe or Phe analog, Trp, Tyr, Leu, HomoLeucine, Ile, and their analogs; aromatic moiety esters or aromatic substitutions of an amino acid; an aromatic, heterocyclic or branched aliphatic moiety; homophenylalanine, homoleucine, glutamic benzyl ester, naphtylalanine.

Due to the peptidomimetic nature of the preferred embodiments according to the invention, the bonds between AAs are not only peptide bonds but may be selected from the group consisting of: an amide, urea, carbamate, hydrazine or sulfonamide bond.

Additional preferred embodiments of the present invention comprise a compound of Formulae IIa-IId:

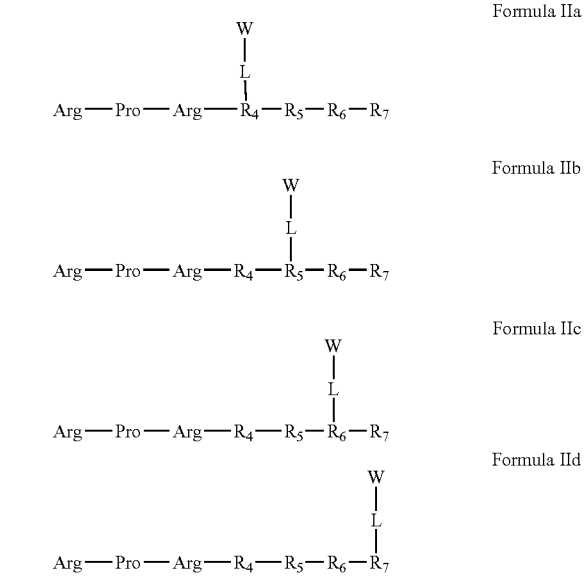

Formula IIa

Formula IIb

Formula IIc

Formula IId wherein:

$R_4$, $R_5$, and $R_6$ are each independently selected from the group consisting of threonine, serine, glutamic acid allyl ester, homocitrulline, lysine, methionine, norleucine, ornithine, arginine, glycine, diaminopropionic acid, diaminobutyric acid, $GlyNH_2$, and alanine; or are an $N^\alpha$-ω-functionalized derivative of an amino acid selected from the group of Glycine, Alanine and Tyrosine;

$R_7$ is selected from the group consisting of phenylalanine, homoleucine, norleucine, glutamic acid allyl ester;

W is absent or is N-(8-sulfonamide-5-isoquinoline) ethylenediamine; and

L may be absent or is selected from the group consisting of glycine, (β-alanine, phenylalanine, aminobutyric acid and aminopentanoic acid.

Preferably, W is connected to $R_5$ as described in Formula IIb.

Currently most preferred embodiments of the present invention include a chimeric compound selected from the compounds described hereinbelow in formulae III-VII:

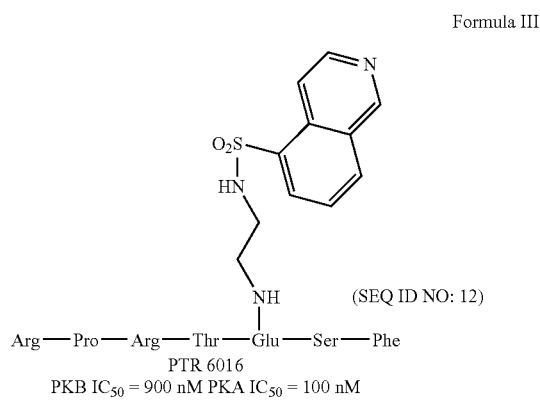

Formula III (SEQ ID NO: 12)

PTR 6016
PKB $IC_{50}$ = 900 nM PKA $IC_{50}$ = 100 nM

-continued

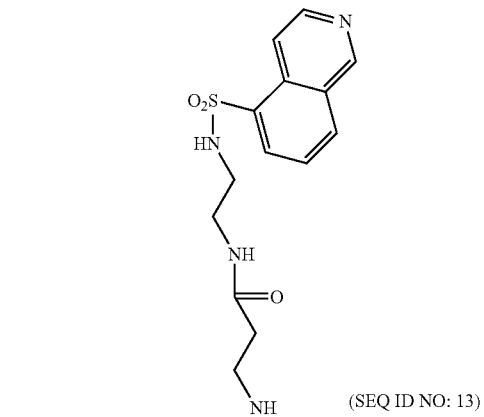

Formula IV (SEQ ID NO: 13)

Arg—Pro—Arg—Nle—Glu—Ser—Phe
PTR 6086
PKB IC$_{50}$ = 570 nM PKA IC$_{50}$ = 500 nM

Formula V

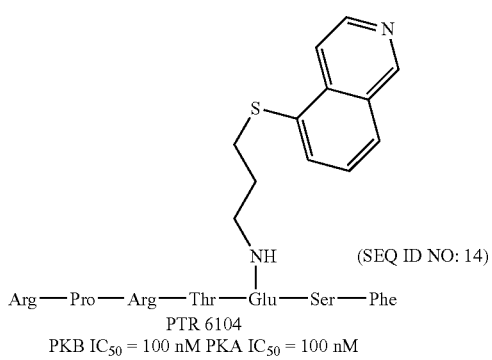

(SEQ ID NO: 14)

Arg—Pro—Arg—Thr—Glu—Ser—Phe
PTR 6104
PKB IC$_{50}$ = 100 nM PKA IC$_{50}$ = 100 nM

Formula VI

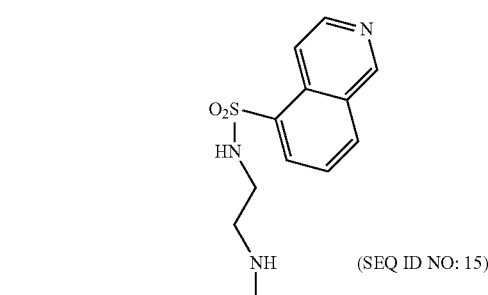

(SEQ ID NO: 15)

Arg—Pro—Arg—Orn—Glu—Ser—Phe
PTR 6132
PKB IC$_{50}$ = 20 nM PKA IC$_{50}$ = 12 nM

-continued

Formula VII

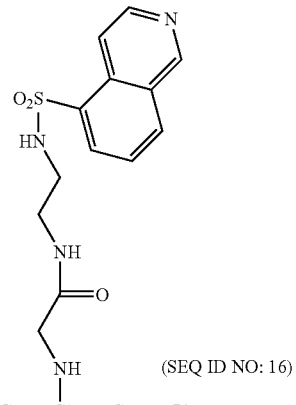

(SEQ ID NO: 16)

Arg—Pro—Arg—Nle—Glu—Ser—Phe
PTR-60020-57
PKB IC$_{50}$ = 70 nM PKA IC$_{50}$ = 210 nM

The activity of the most preferred compounds according to formulae III-VII, as well as additional most preferred embodiments of the present invention, in inhibition of PKB and PKA activity is described in Table 1.

Currently most preferred are compounds comprising a sequence selected from:

Arg-Pro-Arg-Thr-Glu-(bAla-5-mercaptoaminopropyl-isoquinoline)-Ser-Phe (SEQ ID NO: 3).

Arg-Pro-Arg-Thr-Glu-(5-mercaptoaminopropyl-isoquinoline)-Ser-Phe (SEQ ID NO: 4).

Arg-Pro-Arg-Orn-Glu-(5-aminoethylsulfonamide-isoquinoline)-Ser-Phe (SEQ ID NO: 5).

Arg-Pro-Arg-Nva-Glu-(5-mercaptoaminopropyl-isoquinoline)-Ser-Phe (SEQ ID NO: 6).

Arg-Pro-Arg-Nle-Glu-(5-mercaptoaminopropyl-isoquinoline)-Ser-Phe (SEQ ID NO:7).

Arg-Pro-Arg-Orn-Glu-(Gly-5-aminoethylsulfonamide)-Dab-Hol (SEQ ID NO: 8).

Arg-Pro-Arg-Nle-Glu-(Gly-5-aminoethylsulfonamide)-Dab-Phe (SEQ ID NO: 9).

Arg-Pro-Arg-Nle-Glu-(Gly-5-aminoethylsulfonamide)-Dab-Hol (SEQ ID NO: 10).

TABLE 1

Most preferred compounds

| Compound | IC$_{50}$ PKB nM | IC$_{50}$ PKA nM |
| --- | --- | --- |
| PTR 6102 | 300 | 100 |
| PTR 6104 | 100 | 100 |
| PTR 6132 | 20 | 12 |
| PTR 6134 | 217 | 18 |
| PTR 6136 | 114 | 11 |
| TY-60020-42 | 110 | 50 |
| TY-60020-57 | 70 | 210 |
| TY-60020-58 | 120 | 50 |

FIG. 1 describes the synergistic effect of conjugation of the ATP mimic part which poorly inhibit PKB, with the peptide substrate part having activity of 4 μM, to yield the chimeric compound PTR 6016 with activity of 0.9 μM activity.

Additional chimeric compounds comprising active peptides with diverse linkers connecting the peptidic moiety region to the spacer (according to scheme I). The favorable linker enables simultaneous fit of both the peptide and ATP mimic into their substrate and ATP binding sites, and improvement of activity and specificity.

Additional preferred peptides according to the present invention may be uses as the substrate domain of the chimeras and a basis for design of peptidomimetics. For example, linear 7-mer peptides with $IC_{50}$ of 4-5 μM for PKB are disclosed in comparison to the reference 7-mer substrate that has $K_m$ of 15 μm. These peptides are specific to PKB and do not inhibit PKA activity at 60 μM. Additional peptides disclosed demonstrate activity of 0.5-10 μM for inhibition of PKB, and inhibit PKA at an $IC_{50}$ of about 100 nM.

Peptidomimetic compounds having improved stability and cell permeability properties are another embodiment of the present invention. Non-limiting examples of generation of such compounds include N alkylation of selected peptide residues, carbamate, urea and hydrazine bond replacement, and incorporation of hetrocyclic non-peptide moieties such as piperidine, piperazine, pyrrolidine etc. through peptide or non-peptide bond.

General Methods

Synthetic Methods:

General Methods for Synthesis of Peptides and Carbamate Bond Formation.

The following procedure describes the synthesis of peptides in 96 wells plate (MPS plate) at a scale of 6 μmol peptide per well, on Rink amide resin, using bis-(trichloromethyl) carbonate (BTC) for carbamate formation and HBTU/HOBT for normal coupling.

One gram of rink amide 0.6 mmol/g was swelled overnight in NMP with gentle shaking. The resin was distributed into 96 wells plate (~10 mg per well).

Fmoc deprotection performed by adding 500 μl of 25% piperidine solution in NMP to each well and mixing at 650 rpm for 15 min, the piperidine solution is removed by a pressure of nitrogen and another portion of piperidine solution is added and shacked for 15 min. Wash of resin after Fmoc deprotection and after couplings, performed by placing 600 μl NMP into each well, mixing for 2 min. and removing the NMP by nitrogen pressure. The washing procedure is repeated four times.

Regular coupling is performed by adding a solution of Fmoc protected amino acids (150 μl, 0.2M) in HOBT/NMP to the resin, followed by addition of HBTU solution in DMF (150 μl, 0.2M) and DIEA in NMP (150 μl, 0.4M). The reaction vessel block is mixed at 650 rpm for 1 h and then removed by a pressure of nitrogen. This procedure is repeated once.

Carbamate formation using BTC is performed by addition of a solution of Fmoc protected amino alcohols in dioxane (150 μl, 0.2 M), to a preactivation deep well plate, followed by addition of 150 μl BTC (0.07 M) in 1,3-dichloropropane, 150 μl collidine (0.6 M) in 1,3-dichloropropane and 200 μl $CH_2Br_2$. The isocyanate solution is then transferred into the reaction vessel block and mixed for 40 min at 60° C. After 40 min the reaction mixture is removed by nitrogen pressure followed by $CH_2Cl_2$ wash (3×400 μl). This procedure is repeated for additional two times.

Cleavage and global deprotection are performed by transferring the resin from the reaction vessel block into a deep well microtiter plate (cleavage plate). To this plate 350 μl solution of 92.5% TFA, 2.5% $H_2O$, 2.5% TIS, 2.5% EDT is added. The plate is mixed at 1000 rpm for 1 h and then the TFA solution is evaporated to dryness.

Purification by Sep-Pak performed by dissolving the residue of the resin with the peptide in 900 μl solution A (0.1% TFA in water) and applying on C-18 Sep-Pak column. The peptides are eluted from the C-18 column by addition of 900 μl solution $A+CH_3CN$ 1:1 to a deep well plate. The plate is frozen in liquid nitrogen at least 15 min and the peptides are lyophilized General Methods for Synthesis of Chimeras in MPS Format The following procedure describes the synthesis of peptides in 96 wells plate (MPS plate) at a scale of 6 μmol peptide per well, on Rink amide resin, using HBTU/HOBT for normal coupling.

One gram of rink amide 0.6 mmol/g was swelled overnight in No with gentle shaking. The resin was distributed into 96 wells plate (~10 mg per well).

Fmoc deprotection performed by adding 500 μl of 25% piperidine solution in NMP to each well and mixing at 650 rpm for 15 min, the piperidine solution is removed by a pressure of nitrogen and another portion of piperidine solution is added and shacked for 15 min. Wash of resin after Fmoc deprotection and after couplings, performed by placing 600 μl NMP into each well, mixing for 2 min. and removing the NMP by nitrogen pressure. The washing procedure is repeated four times.

Regular coupling is performed by adding a solution of Fmoc protected amino acids (150 μl, 0.2 M) in HOBT/NMP to the resin, followed by addition of HBTU solution in DMF (150 μl, 0.2 M) and DIEA in NMP (150 μl, 0.4 M). The reaction vessel block is mixed at 650 rpm for 1 h and then removed by a pressure of nitrogen. This procedure is repeated once. The last amino acid used in the assembly is N-Boc protected. At the end of assembly allyl deprotection takes place (from Glu(OAllyl) or C-building unit) by placing 500 μl solution of Pd(Pphe3)4 (0.02 M in chloroform containing 5% AcOH÷2.5% NMM and mixing for 1 h. This procedure is repeated once. Wash of the resin after allyl deprotection performed by addition of 600 μl chloroform to each well and mixing for 5 min. The solvent is removed by nitrogen pressure. This wash is repeated for additional four times. The coupling of allyl protected linker to the peptide-resin is carried out by placing allyl protected linker (150 μl, 0.2 M in NMP) followed by addition of PyBoP (0.2 M, in NMP) and DIEA (0.4 M, in NMP). The reaction vessel block is mixed for 1 h the solution is removed by a pressure of nitrogen. This procedure is repeated once. The resin after the coupling is washed by addition of 500 μl NMP to each well. Allyl removal from the linker is carried out followed the same procedure described above. After allyl deprotection, a solution of isoquinoline derivative (150 pd, 0.2 M in NMP) is added followed by addition of ByBoP (150 μl, 0.2 M in NMP) and DMA (150 μl, 0.4 M in NMP). The reaction block is mixed for 2 h.

Wash of the resin after this coupling performed by addition of 600 μl NMP to each well and mixing for 2 min. The solvent is removed by nitrogen pressure. This wash is repeated for additional four times.

Cleavage and global deprotection are performed by transferring the resin from the reaction vessel block into a deep well microtiter plate (cleavage plate). To this plate 350 μl solution of 92.5% TFA, 2.5% $H_2O$, 2.5% TIS, 2.5% EDT is added. The plate is mixed at 1000 rpm for 1 h and then the TFA solution is evaporated to dryness.

Purification by Sep-Pak performed by dissolving the residue of the resin with the peptide in 900 μl solution A (0.1% TFA in water)+CH3CN 1:1 and applying on C-18 Sep-Pak column. This procedure is repeated once more. The plate is frozen in liquid nitrogen at least 15 min and the peptides are lyophilized.

Biological Screening Assays for Inhibition of Protein Kinase Activity:

Cell Free System Methods

In Vitro PKA Kinase Activity Assay.

1. PKA enzyme was purchased from Promega. PKA activity is assayed on a 7-mer peptide, LRRASLG, known as kemptide. The assay is carried out in 96-well plates, in a final volume of 50 µl per well. The reaction mixture includes various concentrations of the inhibitor, 50 mM MOPS, 10 mM MgAc, 0.2 mg/ml BSA, 10 µM ATP, 20 µM Kemptide and 1 µCi $\gamma^{32}$P ATP. Reaction is started with addition of 15 µl of the catalytic subunit of PKA diluted in 0.1 mg/ml BSA, 0.4 U/well. Two blank wells without enzyme are included in every assay. The plates are agitated continuously at 30° C. for 10' or at 27° C. for 1 hour. Reaction is stopped by addition of 12 µl 200 mM EDTA. 20 µl aliquots of the assay mixture are spotted onto 2 cm$^2$ phosphocellulose strips (e.g. Whatman P81) and immersed in 75 mM phosphoric acid (10 ml per sample). The phosphocellulose strips are washed 6 times. Washes are done in continuous swirling for 5 minutes, last wash is in acetone. After air drying the strips, radiation is measured by scintillation spectrometry.

2. Screening compounds for PKA inhibition was performed in 96-well plate using SPA beads, as described below for PKB with the following modifications; The enzyme substrate was 5 µM biotinylated-kemptide peptide (biotin-KLR-RASLG). The kinase buffer was 50 mM MOPS pH 7, 0.2 mg/ml BSA, 10 mM Magnesium acetate. PKA (0.4 unit) diluted in 0.1 mg/ml BSA was added to each well.

PKB In Vitro Kinase Activity Assays.

1. PKB activity is assayed as described in Alessi et al. (FEBS Letters 399, 333, 1996) with the following modifications: instead of HA-PKB coupled to beads, soluble His-HA-PKB is used following precipitation on a Nickel column. The enzyme activity measurement is performed as described in the assay for PKA.

2. Screening compounds for PKB inhibition was performed in 96-well plate using method described previously (Kumar et al, BBA, 1526: 257-268, 2001) with modifications. Kinase reaction was carried out in final volume of 50 µl. Each well contained 2.5 µM of biotinylated-crosstide peptide (biotin-KGRPRTSSFA) in kinase buffer [50 mM Tris-HCl pH 7.5,10 mM Mgca$_2$, 1 mM DTT and 0.1 mM sodium orthovanadate, 0.01% Triton X-100 and 2% dimethyl (Me$_2$SO)], His-PKB enzyme and the potential inhibitory compound. The kinase reaction was started by adding 10 µl of 2 µM cold ATP and 0.25 µCi of [$\gamma^{33}$P]-ATP in kinase buffer. The plates were incubated at 27° C. for 1 hr. At the end of the incubation the reaction was stopped by 200 µl of PBS containing 0.1% Triton X-100, 5 mM EDTA, 1 mM ATP and 0.3 mg/ml of Streptavidin-coated SPA bead (Amersham Pharmacia Biotech). After 15 min incubation at room temperature, the reaction mixtures were filtered using Packard GF/B 96-well plates. The plates were washed twice with 2M NaCl and 1% orthophosphoric acid followed by ethanol wash and 1 h air-dry. The radioactivity was counted using microplate counter Packard Top Count Transfer ELISA Assay for Measuring PKB Activity and Inhibition.

The inhibitor tested is dissolved in water to the desired concentration. Five µl of the inhibitor solution is added to the wells of a V shaped polyproplylene microplate. Five µl of substrate peptide (Biotin-Lys-Gly-Arg-Pro-Arg-Thr-Ser-Ser-Phe-Ala-Glu-Gly (SEQ ID NO: 11)) solution in water at a concentration of 300 µM is then added to the wells (final assay concentration is 100 µM). Then PKB enzyme dissolved in 3.times. reaction m (50 mM Tris HCl pH 7.5, 0.1% beta mercaptoethanol, 1 µM PKI (Calbiochem), 10 mM Mg acetate, ATP 5 µM), is added in pre-calibrated amount to the wells. The amount of enzyme is calibrated so that less than 10% of the substrate is phosphorylated by the end of the reaction as evaluated by mass spectral analysis. The plate is covered with an adhesive tape, placed over a 1 mm ID vortex at 30.degree. C. and incubatd for 30 min to 1 hour as needed. At the end of the incubation period 5 µl of 0.5 M disodium are added to the wells followed by 180 pd of PBS.

For ELISA, a microplate (Costar A/2) is coated with 20 µl of 10 µg/ml of avidin in PBS (over night at 4° C. or 30 minutes at 37° C., on a 1 mm ID vortex). The plate is than washed several times with deionized water and flicked dry on a towel paper. The wells are filled with 20 µl of PBT (PBS+1% BSA+0.05% tween 20). Five µl from the enzyme reaction plate are transferred to the ELISA plate. The ELISA plate in placed on the 1 mm ID vortex and incubated for 10 min at RT. The plate is than washed with water as before. To each well 20 µl of anti phosphopeptide antibody (Cell Signaling Technology) diluted 1:1000 in PBT are added. The plate is placed again on the vortex, incubated for 30 minutes and washed with water as before. To each well 20 µl of goat anti-rabbit Ig conjugate with horse raddish peroxidase (HRP) is added. The plate is placed on the vortex, incubated for 20 min and washed with water as before. To each well is added 20 µl of HRP substrate (Sigmafast OPD). After sufficient color development (up to maximum of about 30 minutes development time) the reaction is terminated by the addition of 20 µl per well of 4 M HCl in water. The plate is than read using an ELISA reader at 490 nm. The signal obtained from wells containing potential inhibitors is compared to signal obtained from wells containing only the enzyme without inhibitor (maximum signal) and wells not containing enzyme (minimum signal).

The fraction of phosphorylated peptide can be also analyzed by mass spectra following desalting on a ziptip (C18, Millipore i). Mass of double charged substrate peptide is 759.3 Dalton, and of the double charged phosphorylated peptide is 799.3 Dalton.

PKC In Vitro Kinase Assays

PKC was obtained from Promega Corp. and assayed according to the manufacturer's instructions using a kit from the same manufacturer, in the presence and absence of phospholipids. The activity of PKC was determined by subtracting the activity in the absence of phospholipids from that in the presence of phospholipids. The concentration of the ATP in the assay was 10 µM (Km for ATP=50 µM).

Assays for Inhibition of PKB Activity in Intact Cells:

Several cancer cell lines were used to determine the activity of PKB inhibitors in intact cells. For example OVCAR3 is a cell line of ovarian carcinoma with an amplification of the PKB gene, U87MG is a glioma cell line with a deletion of PTEN gene—causing high activity of PKB, and PANC1 is a pancreatic carcinoma cell line with an amplification of PKB gene., PC-3, DU-145 and LNCaP are prostate cancer cell lines with alteration in PKB activity.

a. Annexin-V-Apoptosis Assay:

Cells were assayed for apoptosis using the Annexin-V (Bender medsystems). Cells were seeded in 6-well plates (0.3×10$^6$/well) and treated with different concentrations of the inhibitors. At different time point, cells were scraped using rubber policemen, dispensed through syringe needle, washed twice with PBS and suspended in Annexin-V binding buffer (10 mM Hepes/NaOH pH 7.4, 140 mM NaCl and 2.5 mM $CaCl_2$). Annexin-V was diluted 1:40 and added to each sample with 1 µg/ml Propidium Iodide (PI). $0.5 \times 10^6$ cells were taken per sample for FACS analysis for apoptosis measurement In an alternative method, cells were seeded in 10 cm plates ($2 \times 10^6$ cells/plate) and treated with different concentrations of the inhibitor. 40 hours after treatment cells were trypsinysed, washed twice with PBS and suspended in annexin-V buffer, annexin-V (Roche) is diluted 1:250 in a buffer containing. 10 mM HEPES pH 7.4, 140 mM NaCl, 5 mM $CaCl_2$ and 0.2 nM propidium iodid (PI). Apoptosis measurement was performed by FACS analysis.

b. ELISA Assay for Detection of ssDNA—Apoptosis Assay

Cells were assayed for Apoptosis using the ssDNA Apoptosis ELISA kit (Chemicon International Inc.). Cells were seeded in 96-well plates (5000 cells/well) and treated with different concentrations of the inhibitors. At different time point, plates were centrifuges at 200 g for 5 min, medium was removed and the cells were fixed with 80% methanol in PBS for 30 min at room temperature. Plates were dried by floating in a waterbath at 37° C. for 20 minutes. 50 µl of Formamide was added to each well and incubate at room temperature for 10 min. Plates were heated to 75° C. in a circulating waterbath for 10 min, cooled in refrigerator for 5 min, and then formamide was removed. Plates were blocked by 3% non-fat dry milk in distilled water (w/v) for 1 hr at 37° C. Blocking was removed and 100 µl of antibody mixture (primary monoclonal antibody to ssDNA and HRP-labelled anti-mouse IgM) was added to each well. Plates were monitored for colour development by ABTS using microplate reader at 405 nm.

c. Cell Viability Assays:

Cells were seeded in 96-well plates. After 72 hours in culture cells were treated with or without different concentrations (1, 5, 10, 25, 50, 100 µM of the inhibitor, in triplicates for one to six days. Cells viability were tested using three methods: A. staining of viable cells with methylene blue, B. measurement the activity of mitochondrial dehydrogenases in viable cells using WST-1 reagent, c. incorporation of $^3$H-thymidine.

Staining viable cells with methylen blue: Cells were fixed by 0.5% gluterdialdehyde followed by staining with 1% methylene blue in borate buffer (Sigma) for one hour. Cells then washed few times with distilled water, air dried and the color was extracted by adding 0.1 M HCl for one hour at 37° C. Quantitation of color intensity was performed by measurement of the optical density at 620 nm by ELISA reader.

Cell proliferation reagent WST-1: At the appropriate time in culture medium was discarded and 100 µl of WST-1 reagent (Boeheringer mannheim) diluted 1:10 in growth medium was added for 1-2 hours at 37° C. The absorbency of the formazan product was measured at 450 nm with a reference wavelength of 690 nm by microplate ELISA reader.

Incorporation of 3H-thymidine: At the appropriate time in culture luci of 3H-thymidine (stock of 5 Ci/mmole, Amersham) was added to each well containing 100 µl of medium for 5 hours. At the end of the incubation the cells were washed few times with PBS, air dried for few hours and 50 µl of scintillation liquid was added. The radioactivity was counted using microplate counter, Packard TopCount d. Inhibition of Phosphorylation:

Cells ($2 \times 10^6$) were seeded in 25 $cm^2$ flasks grown for 2 days at normal medium conditions then grown for additional 24 hours at starvation conditions (no FCS). At this time point, under starvation conditions, inhibitory compounds were added to analyze their effect on GSK-3 and PKB phosphorylation. At the end of the treatment cells were stimulated for 10 min with 150 µg/ml IGF-1 and lysed using lysis buffer (20 mM Tris-HCl pH 7.4, 150 mM NaCl, 0.5% Triton-x100, 25 mM NaF, 2 mM AEBSF, 1 mM sodium orthovanadate, 10 mM β-glycerophosphate, 1 µg/ml aprotonin and 5 µg/ml leupeptin). Equal amounts of cell protein were resolved by 10% SDS-PAGE and electroblotted to PVDF membranes. Western blot analysis was performed using antibodies against phospho-Akt1 (Ser473), or (Thr 308) and phospho-GSK3α (Ser21) were obtained from Cell Signaling Technology.

In an alternative method, cells were seeded in 6-well plates, and treated with different concentrations of the inhibitor. Treatment was taken either under serum containing media or under starvation for different time periods. After treatment cells are stimulated for 10' with IGF-1 (HEK-293 and PANC1 cells) or EGF (OVCAR3 and U89MG cells). Cell lysates are prepared using boiled sample buffer. Western blot analysis with a phospho-GSK3 showed decrease in GSK3 phosphorylation. The effect was also tested on GSK3 phosphorylation by expression of kinase-dead-PKB in HEK-293 cells.

In Vivo Models for Evaluation the Activity of PKB Inhibitors

The compounds of the present invention are tested for their affect on tumor growth and regression, in xenografs derived from cancerous cell lines such as:
1. Prostate cancer cells PC3, LNCAP and DU145 in nude mice;
2. Ovarian carcinoma cells (OVCAR) in nude mice;
3. Pancreatic cancer cells (PUNC1) in nude mice.

Briefly, the cells are implanted subcutaneously into the animals, and the tumors are allowed to grow to approximately 0.5 mm. The appropriate doses of compounds, which will be determined experimentally by acute toxicity studies, will be injected to the tumor at various stages of its growth. Injection at early stages will reflect the compound's effect on tumor growth, injection into an established tumor will determine its effect on regression. In addition, synergy studies are planned, where the compounds are injected into the tumor along with a known chemotherapy agent, to evaluate synergistic effects resulting from tumor increased sensitivity to chemotherapy due PKB inhibition leading to increased apoptosis.

The skilled artisan will appreciate that the following examples are merely illustrative and serve as non limitative exemplification of the principles of the present invention and that many variations and modifications are possible within the scope of the currently claimed invention as defined by the claims which follow.

EXAMPLES

Example 1

Screening PKA Inhibitors for PKB Inhibition

Since there are no known inhibitors of PKB, the structural similarity between PKB and other protein kinases was used to screen commercially available inhibitors of other protein kinases, e.g., PKA and PKC, for PKB inhibition. The preliminary screen was conducted in order to define some structural motifs in active compounds that would assist in the initial design of a combinatorial library of candidate compounds.

It should be noted, however, that though this approach is very useful for rapid identification of lead molecules, the molecules that are identified would possess inhibition activity against other kinases as well. Thus, this approach dictates research directed not only at optimization of the inhibitory activity, but also, and perhaps most importantly, specificity-oriented research. Namely, substantial efforts are actually directed at modifying the selectivity profile, in order to obtain a profile of selectivity or specificity towards PKB.

The screen yielded two compounds that inhibited PKB in the. 2-3 μM range. H-89, a known PKA inhibitor, was chosen to be the basic scaffold for the design of the first library, based on its structure and on synthetic and specificity considerations.

H-89 was further optimized using rational design and parallel synthesis methods as described in Israeli application No. 136458. It was concluded that the 5-isoquinoline-sulfonamide-ethylenediamine core is essential for activity and replacement with any other core, either as a sulfonamide or a carboxamide derivative, eliminated activity. The substrate mimetic region C was also studied and it what concluded that this region could contain a hydrophobic or heterocyclic moiety or a peptide capable of binding PKB. Outline of these findings is given in the following example. These compounds served as basis for the design of the ATP mimetic moiety of the chimeric compounds according to the present invention.

Example 2

Chimeric Compounds having ATP and Substrate Mimetic Sites

Chimeric molecules are designed to combine an ATP-mimetic together with a substrate-mimetic regions connected via a bridge. These chimeric molecules can bind to both the catalytic site and to the substrate site of protein kinases at the same time and may have a synergistic effect that affords unique potency and selectivity properties. These compounds are designed to include an ATP-mimetic molecule, connected via various spacers to a substrate mimetic portion.

These compounds are identified following synthesis and screening cycles of combinatorial libraries in which each library examines modifications at a different region based on Scheme I, as shown above.

The ATP mimetic core includes but is not limited to dansyls, isoquinolines, quinolines and naphthalenes. The spacer is of varied lengths and conformations of any suitable chemistry including but not limited to amine, amide, thioether, oxyether, sulfonamide bond and the like. Non limiting examples for such spacers include sulfone amide derivatives, amino thiol derivatives and amino alcohol derivatives. The peptidic moiety comprises peptides and peptidomimetics. Such inhibitory peptides may be designed based on any peptide which may serve as a PKB substrate.

Example 3

Detailed Synthesis of Chimeric Compounds

PTR 6013

Four hundred mg of 4-(4-formyl-3-methoxyphenoxy)butyryl (NovaGel HL) were swelled for 1.5 h in dichloroethane/trimethylorthoformate (0.1:1) in a reactor equipped with a sintered glass bottom, attached to a shaker. 352 mg (9 equivalents) of N-(8-sulfonamide-5-isoquinoline)ethylenediamine in 12 ml DMF was added to the resin followed by addition of NaBH(OAc)$_3$ and continues shaking over night. The resin was washed with DMF followed by DCM. Formation of the carbamate bond was performed by addition of Fmoc-Phenyalaninol (291 mg, 5 equivalents) which was preactivated with BTC (77 mg, 1.66 equivalents) and 2,4,6-collidine (290 μl, 14 equivalents) in THF twice at 50° C. Fmoc was removed from the resin using 25% Piperidine in NMP (3 ml) twice for 15 min followed by careful wash, seven times with NMP (5 ml), for 2 min each Assembly of Abu, Ser, Thr, Arg, Pro Arg was accomplished by coupling cycles using Fmoc-Abu-OH, Fmoc-Ser(t-Bu)-OH, Fmoc-Tbr(t-Bu)-OH, Fmoc-Arg(Pmc)-OH, and Fmoc-Pro-OH respectively. In each coupling cycle the amino acid (3 equivalents) was dissolved in NMP and was activated with PyBroP (3 equivalents) and DIEA (6 equivalents). Following coupling, the peptide-resin was washed, than Fmoc was removed followed by extensive wash with NMP, as described above for the first coupling. At the end of the assembly the peptide was cleaved from the resin using 65% TFA, 20% DCM, 5% thioanisole, 3% EDT, 2% TIS and 5% water in a total volume of 7 ml cocktail mixture for 15 min at 0° C. under Argon and then 2 h at room temperature. The solution was filtered through extract filter into polypropylene tube, the resin was washed with 3 ml of 60% TFA in DCM, the combined solution was evaporated by N$_2$ stream to give oily residue which on treatment with cold Et$_2$O solidify. Centrifugation and decantation of the Et$_2$O layer and treatment with additional portion of cold Et$_2$O followed by centrifugation, decantation and drying of the white solid under vacuum over night, gave crude material denoted PTR 6013 having the following structure:

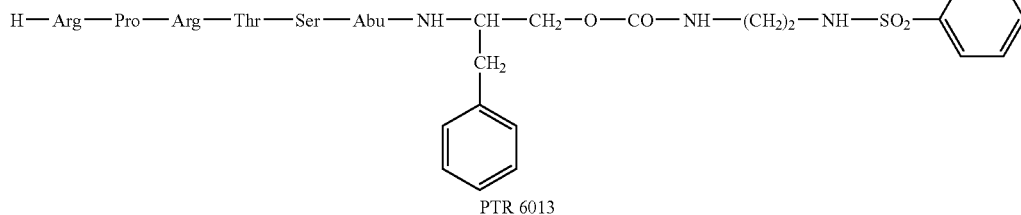

PTR 6013

PTR 6014

Five hundred mg of Rink amide MBHA resin (0.55 mMol/g) were swelled for 2 h in NMP in a reactor equipped with a sintered glass bottom, attached to a shaker. Fmoc was removed from the resin using 25% Piperidine in NMP (4 ml) twice for 15 min followed by careful wash, seven times with NMP (5 ml), for 2 min each Assembly of Phe, Glu, Ser, Thr, Arg, Pro, Arg was accomplished by coupling cycles using Fmoc-Phe-OH, Fmoc-Glu(OAllyl)-OH, Fmoc-Ser(t-Bu)-OH, Fmoc-Thr(t-Bu)-OH, Fmoc-Arg(Pmc)-OH, and Fmoc-Pro-OH respectively. In each coupling cycle, the amino acid (3 equivalents) was dissolved in NMP and was activated with PvBroP (3 equivalents) and DIEA (6 equivalents). At the end of assembly allyl deprotection took place using $Pd(PPh_3)_4$ in solution of $CH_2Cl_2$ containing 5% AcOH and 2.5% NMM. The free acid was activated by 3 equivalents PvBoP and 3.1 equivalents DIEA in NMP for 20 min followed by NMP wash. After preactivation a solution of small molecule (3 equivalents) and DIEA (4.5 equivalents) in NMP was added to the resin and shaken for 1 h at room temperature. Following coupling, the peptide-resin was washed with NMP, than Fmoc was removed followed by extensive wash with NMP, as described above for the first coupling. At the end of the synthesis the peptide was cleaved from the resin using 85% TFA, 5% thioanisole, 3% EDT, 2% TIS and 5% water in a total volume of 5 ml cocktail mixture for 15 min at 0° C. under Argon and then 2 h at room temperature. The solution was filtered through extract filter into polypropylene tube, the resin was washed with 2 ml of TFA. The combined solution was evaporated by $N_2$ stream to give oily residue, which on treatment with cold $Et_2O$ solidifies. Centrifugation and decantation of the $Et_2O$ layer and treatment with additional portion of cold $Et_2O$ followed by centrifugation, decantation and drying the white solid under vacuum over night gave crude material denoted PTR 6014 having the following structure:

equivalents) was dissolved in NMP and was activated with PyBroP (3 equivalents) and DIEA (6 equivalents). At the end of assembly allyl deprotection took place using $Pd(PPh_3)_4$ in solution of $CH_2Cl_2$ containing 5% AcOH and 2.5% M. The free acid was activated by 3 equivalents PyBOP and 3.1 equivalents DIEA in NMP for 20 min followed by NMP wash After preactivation a solution of Allyl γ-aminobutyrate (5 equivalents) and DIEA (6 equivalents) in NMP w as added and shaken for 1 h at room temperature. The allyl deprotection and preactivation was performed by the same procedure as described above. A solution of the small molecule (3 equivalents) and DIEA (4.5 equivalents) in NMP was added to the preactivated peptide-resin and shaken for 1 h at room temperature. Following coupling, the peptide-resin was washed with NMP, than Fmoc was removed followed by extensive wash with NMP, as described above for the first coupling. At the end of the synthesis the peptide was cleaved from the resin using 85% TFA, 5% thioanisole, 3% EDT, 2% TIS and 5% water in a total of 5 ml cocktail mixture for 15 min at 0° C. under Argon and then 2 h at room temperature. The solution was filtered through an extract filter into a polypropylene tube, the resin was washed with 2 ml of TFA, and the combined solution was evaporated by $N_2$ stream to give an oily residue which on treatment with cold $Et_2O$ solidifies. Centrifugation and decantation of the $Et_2O$ layer and treat-

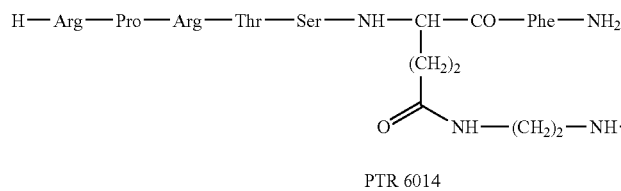

PTR 6014

PTR 6020

Five hundred mg of Rink amide MBHA resin (0.55 mMol/g) were swelled for 2 h in NMP in a reactor equipped with a sintered glass bottom, attached to a shaker. Fmoc was ment with additional portion of cold $Et_2O$ followed by centrifugation, decantation and drying the white solid under vacuum over night gave crude material denoted PTR 6020 having the following structure:

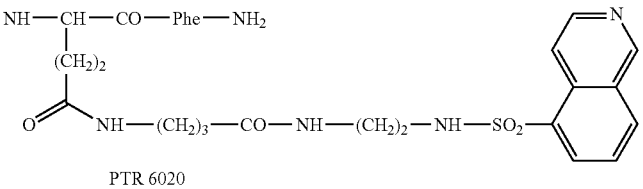

PTR 6020 removed from the resin using 25% piperidine in NMP (4 ml) twice for 15 min followed by careful wash, seven times with NM (5 ml), for 2 min each. Assembly of Phe, Glu, Ser, Thr, Arg, Pro, Arg was accomplished by coupling cycles using Fmoc-Phe-OH, Fmoc-Glu(OAllyl)-OH, Fmoc-Ser(t-Bu)-OH, Fmoc-Thr(t-Bu)-OH, Fmoc-Arg(Pmc)-OH, and Fmoc-Pro-OH respectively. In each coupling cycle the amino acid (3

Example 4

Biological Activity of Chimeric Compounds

Four chimeric compounds were screened for PKB inhibition activity. Table 2 describes their structure and inhibition activities. Similar to the compound denoted B-11-1 these compounds are not specific for PKA.

TABLE 2

| ID # | Activity PKB | Activity PKA |
|---|---|---|
| PTR 6013 | 3 μM | 1 μM |
| PTR 6014 | 25 μM | NA |
| PTR 6016 | 0.9 μM | 0.5 μM |
| PTR 6020 | >20 μM | NA |

Structures of PTR 6013, 6014 and 6020 are described in example 11. The structure of PTR 6016 is:

Formula III

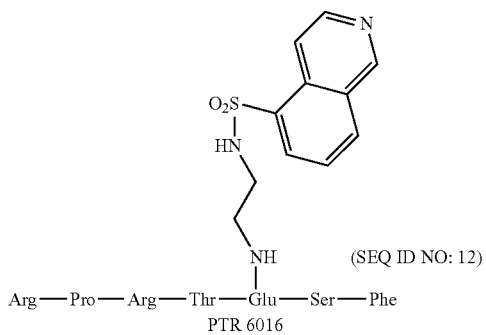

Arg—Pro—Arg—Thr—Glu—Ser—Phe (SEQ ID NO: 12)
PTR 6016

FIG. 1 describes the synergistic effect of conjugation of the ATP mimic part which does not inhibit PKB, with the peptide substrate part having activity of 4 μM, to yield the chimeric compound PTR 6016 with activity of 0.9 μM activity.

Example 5

Additional Chimeric Compounds

A multiple-parallel-synthesis of 96 chimeric compounds of active peptides from plates 60002, 60003 with diverse linkers (L in formulae II) connecting the peptide to the small molecule (W in Formulae II) was performed. These peptides were designed for elucidating the appropriate linker which enables simultaneous fit of both the peptide and ATP mimic into their substrate and ATP binding sites, for improving activity and specificity.

The compounds synthesized are described in formulae IIa-IId, as specified above.

Example 6

Peptides

Additional peptides are designed for use in the substrate domain of the chimeras and for design of peptidomimetics. Two plates of linear 7-mer peptides were synthesized and purified. Four peptides from the first plate (6002) were found to be active with IC$_{50}$ of 4-5 μM for PKB (the reference 7-mer substrate has IC$_{50}$ of 15 μm. All these peptides do not inhibit PKA activity at 60 μM. From the second plate (6003)~24 active peptides were identified, peptides exhibiting >60% inhibition were tested again, demonstrating activity of 0.5-10 μM for PKB. Specificity to PKA not tested yet Additional 1152 peptides from macrobeads library were screened, 150 had over 50% inhibition at 10 μM. Three multiple-parallel-synthesis plates were then planed and synthesized. Selected results are presented in the following table.

TABLE 3

| ID | Structure | | Activity PKB | Activity PKA |
|---|---|---|---|---|
| TY 60002-50: | Arg-Pro-Arg-Thr-Ser-Ala-Hol | (SEQ ID NO: 17) | 5 μM | >40 μM |
| TY 60002-61: | Arg-Pro-Arg-Val-Ser-Abu-Phe | (SEQ ID NO: 18) | 5 μM | >40 μM |
| TY 60002-73: | Arg-Pro-Arg-Thr-Ser-Abu-Hol | (SEQ ID NO: 19) | 5 μM | >40 μM |
| TY 60002-96: | Arg-Pro-Arg-Thr-Ser-Dap-Hol | (SEQ ID NO: 20) | 5 μM | >40 μM |
| TY 60002-18 | Arg-Pro-Arg-Thr-Ser-Asp-Phe | (SEQ ID NO: 21) | Not active | |
| AR 60003-50: | Arg-Pro-Arg-Met-Ser-Ser-Phe | (SEQ ID NO: 22) | 2.5 μM | |
| AR 60003-52: | Arg-Pro-Arg-Orn-Ser-Ser-Phe | (SEQ ID NO: 23) | 2.5 μM | |
| AR 60003-53: | Arg-Pro-Arg-Arg-Ser-Ser-Phe | (SEQ ID NO: 24) | 3 μM | |
| AR 60003-62: | Arg-Pro-Arg-Nle-Ser-Ser-Nle | (SEQ ID NO: 25) | <1 μM (70% inhibition at 1 μM) | |
| AR 60003-64 | Arg-Pro-Arg-Arg-Ser-Ser-Arg | (SEQ ID NO: 26) | Not active | |
| AR 60003-96 | Arg-Pro-Arg-Orn-Ala-Thr-Orn | (SEQ ID NO: 27) | Not active | |

Figure 2:
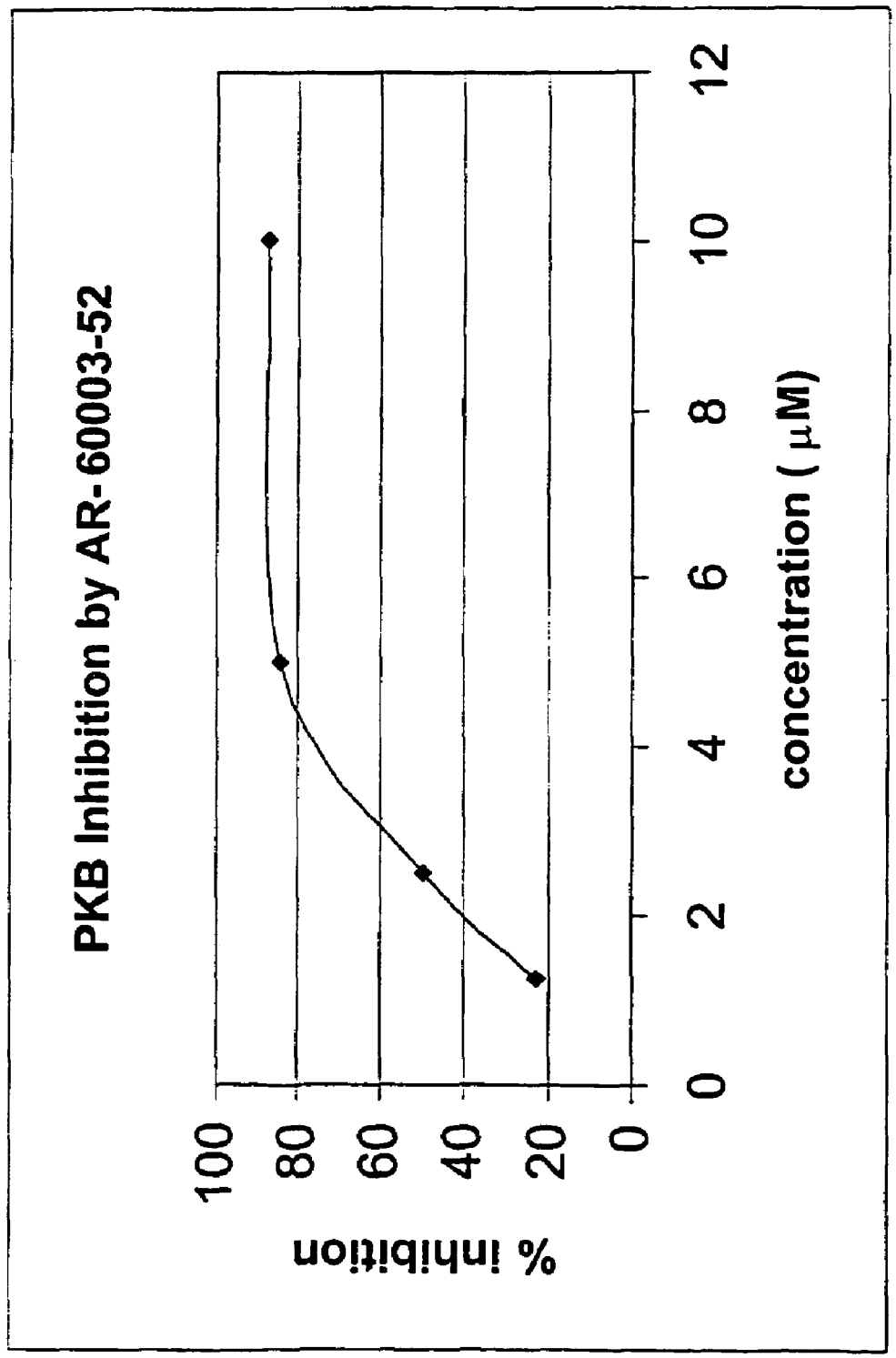
FIG. 2. Inhibition activity curve for AR-60003-52 as described in example 6.

The PKB inhibition activity of peptide AR-60003-52 as determined in ELISA is illustrated in FIG. 2.

Example 7

Peptidomimetic Compounds Based on the Active Peptides

The following peptidomimetic compounds which contain carbamate and/or urea bonds replacing peptidic bonds, were synthesized.

PTR 6046: H-Arg-NH—(CH$_2$)$_2$—H—CO-Arg-Thr-Ser-Dap-Hol-NH$_2$

PTR 6048: H-Arg-NH—CH$_2$—C$_6$H$_4$—CH$_2$—NH—CO-Arg-Thr-Ser-Dap-Hol-NH$_2$

PTR 6050: H$_2$N—(CH$_2$)$_4$—NH—CO-Pro-Arg-Thr-Ser-Dap-Hol-NH$_2$

PTR 6052: $H_2N—(CH_2)_4—NH—CO-3-(HNCH_2)—C_6H_4—CH_2NH—CO$-Arg-Thr-Ser-Dap-Hol-$NH_2$

PTR 6054: H-ArgOl-NH—$CH_2$—$C_6H_4$—$CH_2$NH—CO-Arg-Thr-Ser-Dap-Hol-$NH_2$ (this compound contains both carbamate and urea bonds).

PTR 6056: H-Arg-1,4-Homopiperazine-CO-Arg-Thr-Ser-Dap-Hol-$NH_2$

Example 8

Detailed Synthesis of PTR 6046, an Heptamer Containing an Urea Bond

One hundred mg (0.055 μmol) of rink amide resin were swelled 1.5 h in NMP in a reactor with a sintered glass bottom, attached to a shaker. Fmoc was removed from the resin using 25% piperidine in NMP (3 ml) twice for 15 min followed by careful wash, seven times with NMP (2 ml). Assembly of Arg-Thr-Ser-Dap-Hol was accomplished by coupling cycles using Fmoc-Hol-OH, Fmoc-Dap-OH, Fmoc-Ser(t-Bu)-OH, Fmoc-Thr(t-Bu)-OH, Fmoc-Arg(Pmc)-OH. In each coupling cycle the amino acid (3 equivalents) was dissolved in NMP and was activated with PyBroP (3 equivalents) and DIEA (6 equivalents). Following coupling, the peptide-resin was washed, than Fmoc was removed followed by extensive wash with NMP.

Formation of the Urea Bond:

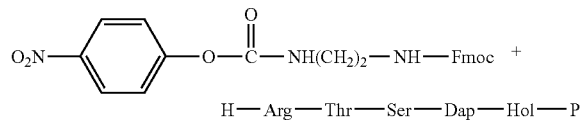

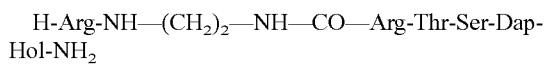

50 mg (2 equivalents) of N-Fluorenylmethoxycarbonyl-N'-nitrophenoxycarbonyl-diaminoethane, 25 μl (2.5 equivalents) of DIEA in 2 ml NMP was added to the resin and continues shaking 1.5 h. The resin was washed with NMP (5 times 2 min each). After formation of the urea bond, a coupling of Fmoc-Arg(Pmc)-OH was performed as describe above followed by Fmoc deprotection. At the end of the assembly the peptide was cleaved from the resin using 92.5% TFA, 2.5% EDT, 2.5% TIS and 2.5% water in a total volume of 5 ml cocktail mixture and continues shaking 1 h. The solution was filtered through extract filter into polypropylene tube, the resin was washed with 2 ml of TFA, the combined solution was evaporated by $N_2$ stream to give oily residue which on treatment with cold $Et_2O$ solidify. Centrifugation and decantation of the $Et_2O$ layer and treatment with additional portion of cold $Et_2O$ followed by centrifugation and decantation and drying the white solid under vacuum over night gave crude PTR 6046 having the following structure:

H-Arg-NH—$(CH_2)_2$—NH—CO—Arg-Thr-Ser-Dap-Hol-$NH_2$

Example 9

Synthesis and Screening of 96 Chimeric Compounds in MPS Format

The following sequences (denoted TY-60020- and shown in Table 4) were synthesized in MPS format according to the synthesis method above.

TABLE 4

Structure of compounds in TY-60020 plate

| | 1 | 2 | 3 | 4 | 5 | Linker* | ATP mimetic | 6 | 7 |
|---|---|---|---|---|---|---|---|---|---|
| 1 | Arg | Pro | Arg | Dap | Glu | 0 | 5-aminoethylsulfonamide isoquinoline | Dab | Phe |
| 2 | Arg | Pro | Arg | Dap | Glu | 0 | 5-aminoethylsulfonamide isoquinoline | Dab | Hol |
| 3 | Arg | Pro | Arg | Dap | Glu | 0 | 5-aminoethylsulfonamide isoquinoline | Orn | Phe |
| 4 | Arg | Pro | Arg | Dap | Glu | 0 | 5-aminoethylsulfonamide isoquinoline | Orn | Hol |
| 5 | Arg | Pro | Arg | Dap | Glu | 0 | 5-aminoethylsulfonamide isoquinoline | Ala | Phe |
| 6 | Arg | Pro | Arg | Dap | Glu | 0 | 5-aminoethylsulfonamide isoquinoline | Ala | Hol |
| 7 | Arg | Pro | Arg | Dap | Glu | 0 | 5-aminoethylsulfonamide isoquinoline | Nva | Phe |
| 8 | Arg | Pro | Arg | Dap | Glu | 0 | 5-aminoethylsulfonamide isoquinoline | Nva | Hol |
| 9 | Arg | Pro | Arg | Orn | Glu | 0 | 5-aminoethylsulfonamide isoquinoline | Dab | Phe |
| 10 | Arg | Pro | Arg | Orn | Glu | 0 | 5-aminoethylsulfonamide isoquinoline | Dab | Hol |
| 11 | Arg | Pro | Arg | Orn | Glu | 0 | 5-aminoethylsulfonamide isoquinoline | Orn | Phe |
| 12 | Arg | Pro | Arg | Orn | Glu | 0 | 5-aminoethylsulfonamide isoquinoline | Orn | Hol |
| 13 | Arg | Pro | Arg | Orn | Glu | 0 | 5-aminoethylsulfonamide isoquinoline | Ala | Phe |
| 14 | Arg | Pro | Arg | Orn | Glu | 0 | 5-aminoethylsulfonamide isoquinoline | Ala | Hol |
| 15 | Arg | Pro | Arg | Orn | Glu | 0 | 5-aminoethylsulfonamide isoquinoline | Nva | Phe |

TABLE 4-continued

Structure of compounds in TY-60020 plate

| | 1 | 2 | 3 | 4 | 5 | Linker* | ATP mimetic | 6 | 7 |
|---|---|---|---|---|---|---|---|---|---|
| 16 | Arg | Pro | Arg | Orn | Glu | 0 | 5-aminoethylsulfonamide isoquinoline | Nva | Hol |
| 17 | Arg | Pro | Arg | Abu | Glu | 0 | 5-aminoethylsulfonamide isoquinoline | Dab | Phe |
| 18 | Arg | Pro | Arg | Abu | Glu | 0 | 5-aminoethylsulfonamide isoquinoline | Dab | Hol |
| 19 | Arg | Pro | Arg | Abu | Glu | 0 | 5-aminoethylsulfonamide isoquinoline | Orn | Phe |
| 20 | Arg | Pro | Arg | Abu | Glu | 0 | 5-aminoethylsulfonamide isoquinoline | Orn | Hol |
| 21 | Arg | Pro | Arg | Abu | Glu | 0 | 5-aminoethylsulfonamide isoquinoline | Ala | Phe |
| 22 | Arg | Pro | Arg | Abu | Glu | 0 | 5-aminoethylsulfonamide isoquinoline | Ala | Hol |
| 23 | Arg | Pro | Arg | Abu | Glu | 0 | 5-aminoethylsulfonamide isoquinoline | Nva | Phe |
| 24 | Arg | Pro | Arg | Abu | Glu | 0 | 5-aminoethylsulfonamide isoquinoline | Nva | Hol |
| 25 | Arg | Pro | Arg | Nle | Glu | 0 | 5-aminoethylsulfoneamide isoquinoline | Dab | Phe |
| 26 | Arg | Pro | Arg | Nle | Glu | 0 | 5-aminoethylsulfonamide isoquinoline | Dab | Hol |
| 27 | Arg | Pro | Arg | Nle | Glu | 0 | 5-aminoethylsulfonamide isoquinoline | Orn | Phe |
| 28 | Arg | Pro | Arg | Nle | Glu | 0 | 5-aminoethylsulfonamide isoquinoline | Orn | Hol |
| 29 | Arg | Pro | Arg | Nle | Glu | 0 | 5-aminoethylsulfonamide isoquinoline | Ala | Phe |
| 30 | Arg | Pro | Arg | Nle | Glu | 0 | 5-aminoethylsulfonamide isoquinoline | Ala | Hol |
| 31 | Arg | Pro | Arg | Nle | Glu | 0 | 5-aminoethylsulfonamide isoquinoline | Nva | Phe |
| 32 | Arg | Pro | Arg | Nle | Glu | 0 | 5-aminoethylsulfonamide isoquinoline | Nva | Hol |
| 33 | Arg | Pro | Arg | Dap | Glu | Gly | 5-aminoethylsulfonamide isoquinoline | Dab | Phe |
| 34 | Arg | Pro | Arg | Dap | Glu | Gly | 5-aminoethylsulfoneamide isoquinoline | Dab | Hol |
| 35 | Arg | Pro | Arg | Dap | Glu | Gly | 5-aminoethylsulfoneamide isoquinoline | Orn | Phe |
| 36 | Arg | Pro | Arg | Dap | Glu | Gly | 5-aminoethylsulfoneamide isoquinoline | Orn | Hol |
| 37 | Arg | Pro | Arg | Dap | Glu | Gly | 5-aminoethylsulfoneamide isoquinoline | Ala | Phe |
| 38 | Arg | Pro | Arg | Dap | Glu | Gly | 5-aminoethylsulfoneamide isoquinoline | Ala | Hol |
| 39 | Arg | Pro | Arg | Dap | Glu | Gly | 5-aminoethylsulfoneamide isoquinoline | Nva | Phe |
| 40 | Arg | Pro | Arg | Dap | Glu | Gly | 5-aminoethylsulfoneamide isoquinoline | Nva | Hol |
| 41 | Arg | Pro | Arg | Orn | Glu | Gly | 5-aminoethylsulfoneamide isoquinoline | Dab | Phe |
| 42 | Arg | Pro | Arg | Orn | Glu | Gly | 5-aminoethylsulfoneamide isoquinoline | Dab | Hol |
| 43 | Arg | Pro | Arg | Orn | Glu | Gly | 5-aminoethylsulfoneamide isoquinoline | Orn | Phe |
| 44 | Arg | Pro | Arg | Orn | Glu | Gly | 5-aminoethylsulfoneamide isoquinoline | Orn | Hol |
| 45 | Arg | Pro | Arg | Orn | Glu | Gly | 5-aminoethylsulfoneamide isoquinoline | Ala | Phe |
| 46 | Arg | Pro | Arg | Orn | Glu | Gly | 5-aminoethylsulfoneamide isoquinoline | Ala | Hol |
| 47 | Arg | Pro | Arg | Orn | Glu | Gly | 5-aminoethylsulfoneamide isoquinoline | Nva | Phe |
| 48 | Arg | Pro | Arg | Orn | Glu | Gly | 5-aminoethylsulfoneamide isoquinoline | Nva | Hol |
| 49 | Arg | Pro | Arg | Abu | Glu | Gly | 5-aminoethylsulfoneamide isoquinoline | Dab | Phe |
| 50 | Arg | Pro | Arg | Abu | Glu | Gly | 5-aminoethylsulfoneamide isoquinoline | Dab | Hol |
| 51 | Arg | Pro | Arg | Abu | Glu | Gly | 5-aminoethylsulfoneamide isoquinoline | Orn | Phe |
| 52 | Arg | Pro | Arg | Abu | Glu | Gly | 5-aminoethylsulfoneamide isoquinoline | Orn | Hol |

TABLE 4-continued

Structure of compounds in TY-60020 plate

| | 1 | 2 | 3 | 4 | 5 | Linker* | ATP mimetic | 6 | 7 |
|---|---|---|---|---|---|---|---|---|---|
| 53 | Arg | Pro | Arg | Abu | Glu | Gly | 5-aminoethylsulfoneamide isoquinoline | Ala | Phe |
| 54 | Arg | Pro | Arg | Abu | Glu | Gly | 5-aminoethylsulfoneamide isoquinoline | Ala | Hol |
| 55 | Arg | Pro | Arg | Abu | Glu | Gly | 5-aminoethylsulfoneamide isoquinoline | Nva | Phe |
| 56 | Arg | Pro | Arg | Abu | Glu | Gly | 5-aminoethylsulfoneamide isoquinoline | Nva | Hol |
| 57 | Arg | Pro | Arg | Nle | Glu | Gly | 5-aminoethylsulfoneamide isoquinoline | Dab | Phe |
| 58 | Arg | Pro | Arg | Nle | Glu | Gly | 5-aminoethylsulfoneamide isoquinoline | Dab | Hol |
| 59 | Arg | Pro | Arg | Nle | Glu | Gly | 5-aminoethylsulfoneamide isoquinoline | Orn | Phe |
| 60 | Arg | Pro | Arg | Nle | Glu | Gly | 5-aminoethylsulfoneamide isoquinoline | Orn | Hol |
| 61 | Arg | Pro | Arg | Nle | Glu | Gly | 5-aminoethylsulfoneamide isoquinoline | Ala | Phe |
| 62 | Arg | Pro | Arg | Nle | Glu | Gly | 5-aminoethylsulfoneamide isoquinoline | Ala | Hol |
| 63 | Arg | Pro | Arg | Nle | Glu | Gly | 5-aminoethylsulfoneamide isoquinoline | Nva | Phe |
| 64 | Arg | Pro | Arg | Nle | Glu | Gly | 5-aminoethylsulfoneamide isoquinoline | Nva | Hol |
| 65 | Arg | Pro | Arg | Dap | Glu | bAla | 5-aminoethylsulfoneamide isoquinoline | Dab | Phe |
| 66 | Arg | Pro | Arg | Dap | Glu | bAla | 5-aminoethylsulfoneamide isoquinoline | Dab | Hol |
| 67 | Arg | Pro | Arg | Dap | Glu | bAla | 5-aminoethylsulfoneamide isoquinoline | Orn | Phe |
| 68 | Arg | Pro | Arg | Dap | Glu | bAla | 5-aminoethylsulfoneamide isoquinoline | Orn | Hol |
| 69 | Arg | Pro | Arg | Dap | Glu | bAla | 5-aminoethylsulfoneamide isoquinoline | Ala | Phe |
| 70 | Arg | Pro | Arg | Dap | Glu | bAla | 5-aminoethylsulfoneamide isoquinoline | Ala | Hol |
| 71 | Arg | Pro | Arg | Dap | Glu | bAla | 5-aminoethylsulfoneamide isoquinoline | Nva | Phe |
| 72 | Arg | Pro | Arg | Dap | Glu | bAla | 5-aminoethylsulfoneamide isoquinoline | Nva | Hol |
| 73 | Arg | Pro | Arg | Orn | Glu | bAla | 5-aminoethylsulfoneamide isoquinoline | Dab | Phe |
| 74 | Arg | Pro | Arg | Orn | Glu | bAla | 5-aminoethylsulfoneamide isoquinoline | Dab | Hol |
| 75 | Arg | Pro | Arg | Orn | Glu | bAla | 5-aminoethylsulfoneamide isoquinoline | Orn | Phe |
| 76 | Arg | Pro | Arg | Orn | Glu | bAla | 5-aminoethylsulfoneamide isoquinoline | Orn | Hol |
| 77 | Arg | Pro | Arg | Orn | Glu | bAla | 5-aminoethylsulfoneamide isoquinoline | Ala | Phe |
| 78 | Arg | Pro | Arg | Orn | Glu | bAla | 5-aminoethylsulfoneamide isoquinoline | Ala | Hol |
| 79 | Arg | Pro | Arg | Orn | Glu | bAla | 5-aminoethylsulfoneamide isoquinoline | Nva | Phe |
| 80 | Arg | Pro | Arg | Orn | Glu | bAla | 5-aminoethylsulfoneamide isoquinoline | Nva | Hol |
| 81 | Arg | Pro | Arg | Abu | Glu | bAla | 5-aminoethylsulfoneamide isoquinoline | Dab | Phe |
| 82 | Arg | Pro | Arg | Abu | Glu | bAla | 5-aminoethylsulfoneamide isoquinoline | Dab | Hol |
| 83 | Arg | Pro | Arg | Abu | Glu | bAla | 5-aminoethylsulfoneamide isoquinoline | Orn | Phe |
| 84 | Arg | Pro | Arg | Abu | Glu | bAla | 5-aminoethylsulfoneamide isoquinoline | Orn | Hol |
| 85 | Arg | Pro | Arg | Abu | Glu | bAla | 5-aminoethylsulfoneamide isoquinoline | Ala | Phe |
| 86 | Arg | Pro | Arg | Abu | Glu | bAla | 5-aminoethylsulfoneamide isoquinoline | Ala | Hol |
| 87 | Arg | Pro | Arg | Abu | Glu | bAla | 5-aminoethylsulfoneamide isoquinoline | Nva | Phe |
| 88 | Arg | Pro | Arg | Abu | Glu | bAla | 5-aminoethylsulfoneamide isoquinoline | Nva | Hol |
| 89 | Arg | Pro | Arg | Nle | Glu | bAla | 5-aminoethylsulfoneamide isoquinoline | Dab | Phe |

TABLE 4-continued

Structure of compounds in TY-60020 plate

| | 1 | 2 | 3 | 4 | 5 | Linker* | ATP mimetic | 6 | 7 |
|---|---|---|---|---|---|---|---|---|---|
| 90 | Arg | Pro | Arg | Nle | Glu | bAla | 5-aminoethylsulfoneamide isoquinoline | Dab | Hol |
| 91 | Arg | Pro | Arg | Nle | Glu | bAla | 5-aminoethylsulfoneamide isoquinoline | Orn | Phe |
| 92 | Arg | Pro | Arg | Nle | Glu | bAla | 5-aminoethylsulfoneamide isoquinoline | Orn | Hol |
| 93 | Arg | Pro | Arg | Nle | Glu | bAla | 5-aminoethylsulfoneamide isoquinoline | Ala | Phe |
| 94 | Arg | Pro | Arg | Nle | Glu | bAla | 5-aminoethylsulfoneamide isoquinoline | Ala | Hol |
| 95 | Arg | Pro | Arg | Nle | Glu | bAla | 5-aminoethylsulfoneamide isoquinoline | Nva | Phe |
| 96 | Arg | Pro | Arg | Nle | Glu | bAla | 5-aminoethylsulfoneamide isoquinoline | Nva | Hol |

*The ATP mimetic is connected via the specified linker to the carboxy group of the glutamic acid side chain at position 5.

The 96 compounds were screened at 1 µM compound concentration (according to the above methods) for PKB and PKA activity inhibition (% inhibition of kinase activity) and the results are summarized in Table 5:

TABLE 5

Screening results of TY-60020 compounds

| Sample # | PKB-kinase (spa) | | PKA-kinase | |
|---|---|---|---|---|
| | Assay 1 | Assay 2 | Assay 1 | Assay 2 |
| 60020-1 | 67 | 65 | 98 | 99 |
| 60020-2 | 47 | 48 | 94 | 95 |
| 60020-3 | 52 | 60 | 96 | 96 |
| 60020-4 | 34 | 53 | | |
| 60020-5 | 46 | 26 | | |
| 60020-6 | 32 | 14 | | |
| 60020-8 | 18 | 0 | | |
| 60020-9 | 71 | 57 | 96 | 97 |
| 60020-10 | 45 | 48 | 92 | 94 |
| 60020-11 | 58 | 52 | 95 | 96 |
| 60020-12 | 23 | 3 | | |
| 60020-13 | 36 | 29 | | |
| 60020-14 | 26 | 31 | | |
| 60020-15 | 31 | 44 | | |
| 60020-17 | 34 | 38 | | |
| 60020-18 | 18 | 28 | | |
| 60020-19 | 32 | 26 | | |
| 60020-20 | 11 | 15 | | |
| 60020-21 | −2 | 6 | | |
| 60020-22 | −5 | −2 | | |
| 60020-23 | −3 | −8 | | |
| 60020-24 | −17 | −12 | | |
| 60020-26 | 17 | 18 | | |
| 60020-27 | 63 | 25 | | |
| 60020-28 | 27 | 31 | | |
| 60020-29 | 19 | 39 | | |
| 60020-30 | 14 | 38 | | |
| 60020-32 | 12 | 32 | | |
| 60020-33 | 63 | 69 | 98 | 98 |
| 60020-34 | 64 | 65 | 97 | 98 |
| 60020-35 | 43 | 56 | 95 | 96 |
| 60020-36 | 69 | 71 | 93 | 94 |
| 60020-37 | 53 | 44 | 98 | 99 |
| 60020-38 | 49 | 49 | 98 | 99 |
| 60020-39 | 17 | 16 | | |
| 60020-40 | 36 | 22 | | |
| 60020-42 | 80 | 86 | 99 | 99 |
| 60020-43 | 48 | 62 | 96 | 96 |
| 60020-44 | 54 | 67 | 95 | 95 |
| 60020-45 | 29 | 53 | | |
| 60020-46 | 37 | 57 | | |
| 60020-47 | 21 | 33 | | |
| 60020-48 | 10 | 22 | | |
| 60020-49 | 66 | 66 | 95 | 95 |
| 60020-50 | 60 | 54 | 97 | 97 |
| 60020-51 | 47 | 37 | 94 | 95 |
| 60020-52 | 56 | 53 | 92 | 92 |
| 60020-53 | 20 | 13 | | |
| 60020-54 | 34 | 45 | | |
| 60020-55 | 20 | 40 | | |
| 60020-56 | 20 | 47 | | |
| 60020-57 | 92 | 93 | 95 | 96 |
| 60020-58 | 89 | 93 | 98 | 99 |
| 60020-59 | 62 | 75 | 92 | 93 |
| 60020-60 | 59 | 70 | 87 | 89 |
| 60020-61 | 29 | 40 | | |
| 60020-62 | 29 | 38 | | |
| 60020-63 | 17 | 19 | | |
| 60020-64 | 25 | 26 | | |
| 60020-65 | 32 | 30 | | |
| 60020-66 | 52 | 63 | | |
| 60020-67 | 51 | 68 | | |
| 60020-68 | 61 | 74 | | |
| 60020-69 | 36 | 57 | | |
| 60020-70 | 57 | 68 | | |
| 60020-71 | 32 | 46 | | |
| 60020-72 | 31 | 52 | | |
| 60020-73 | 16 | 35 | | |
| 60020-74 | 33 | 41 | | |
| 60020-75 | 23 | 35 | | |
| 60020-76 | 38 | 38 | | |
| 60020-77 | 13 | 15 | | |
| 60020-78 | 21 | 24 | | |
| 60020-80 | 13 | 35 | | |
| 60020-16 | 5 | 37 | | |
| 60020-81 | −17 | 42 | | |
| 60020-82 | −9 | 56 | | |
| 60020-83 | −21 | 60 | | |
| 60020-84 | 10 | 51 | | |
| 60020-85 | −27 | −2 | | |
| 60020-86 | −55 | −5 | | |
| 60020-87 | −50 | 5 | | |
| 60020-88 | −50 | 31 | | |
| 60020-89 | 8 | 48 | | |
| 60020-90 | 19 | 27 | | |

TABLE 5-continued

Screening results of TY-60020 compounds

| Sample # | PKB-kinase (spa) | | PKA-kinase | |
|---|---|---|---|---|
| | Assay 1 | Assay 2 | Assay 1 | Assay 2 |
| 60020-92 | 40 | 59 | | |
| 60020-93 | −12 | 58 | | |
| 60020-94 | 9 | 31 | | |
| 60020-95 | 46 | 90 | | |
| 60020-96 | 0 | 54 | | |

TABLE 6 most active compounds from plate TY-60020

| Compound | $IC_{50}$ PKB nM | $IC_{50}$ PKA nM |
|---|---|---|
| TY-60020-57 | 70 | 210 |
| TY-60020-58 | 120 | 50 |
| TY-60020-42 | 110 | 50 |
| TY-60020-95 | 3300 | 2000 |
| TY-60020-67 | 1080 | 250 |
| TY-60020-68 | 500 | 250 |
| TY-60020-59 | 300 | 200 |

Example 10

Synthesis of 19 Chimeric Compounds

Additional 19 compound were synthesized (denoted BP-60023-) comprising $N^\alpha$-ω-functionalized derivative of an amino acid at position 5 incorporated in order to adjust the spatial position of the peptide and the small molecule relative to each other, by attachment to N-derivatized amino acid rather than to amino acid side chain. The sequences are shown in Table 7.

TABLE 7

MPS plate BP-60023

| | 1 | 2 | 3 | 4 | 5 | 6 | 7 |
|---|---|---|---|---|---|---|---|
| 1 | CO-N-SO2-IQ | Arg | Pro | Arg | Nva | DTyrC4* | Dap | Hol |
| 2 | CO-N-SO2-IQ | Arg | Pro | Arg | Orn | DTyrC4* | Dap | Hol |
| 3 | CO-N-SO2-IQ | Arg | Pro | Arg | Nva | TyrC4* | Dap | Hol |
| 4 | CO-N-SO2-IQ | Arg | Pro | Arg | Orn | LTyrC4* | Dap | Hol |
| 5 | CO-N-SO2-IQ | Arg | Pro | Arg | Orn | GlyC2* | Ser | Phe |
| 6 | CO-N-SO2-IQ | Arg | Pro | Arg | Orn | GlyC3* | Ser | Phe |
| 7 | CO-N-SO2-IQ | Arg | Pro | Arg | Orn | GlyC5* | Ser | Phe |
| 8 | CO-N-SO2-IQ | Arg | Pro | Arg | Nle | GlyC2* | Dab | Phe |
| 9 | CO-N-SO2-IQ | Arg | Pro | Arg | Nle | GlyC3* | Dab | Phe |
| 10 | CO-N-SO2-IQ | Arg | Pro | Arg | Nle | GlyC5* | Dab | Phe |
| 11 | CO-N-SO2-IQ | Arg | Pro | Arg | Orn | GlyC2* | Dab | Phe |
| 12 | CO-N-SO2-IQ | Arg | Pro | Arg | Orn | GlyC3* | Dab | Phe |
| 13 | CO-N-SO2-IQ | Arg | Pro | Arg | Orn | GlyC5* | Dab | Phe |
| 14 | CO-N-SO2-IQ | Arg | Pro | Arg | Orn | GlyC2* | Dab | Hol |
| 15 | CO-N-SO2-IQ | Arg | Pro | Arg | Orn | GlyC3* | Dab | Hol |
| 16 | CO-N-SO2-IQ | Arg | Pro | Arg | Orn | GlyC5* | Dab | Hol |
| 17 | CO-N-SO2-IQ | Arg | Pro | Arg | Nva | GlyC2* | Ala | Hol |
| 18 | CO-N-SO2-IQ | Arg | Pro | Arg | Nva | GlyC3* | Ala | Hol |
| 19 | CO-N-SO2-IQ | Arg | Pro | Arg | Nva | GlyC5* | Ala | Hol |

SO2-IQ = 5-aminoethylsulfoneamide isoquinoline

Example 11

Structure and Activity of Chimeric PTRs

TABLE 8

| PTR | Structure | | PKB $IC_{50}$ (uM) | PKA $IC_{50}$ (uM) |
|---|---|---|---|---|
| 6013: | Arg-Pro-Arg-Thr-Ser-Abu-Phe-(O-CO-N-SO2-IQ) | (SEQ ID NO: 28) | 4 | na |
| 6014: | Arg-Pro-Arg-Thr-Ser-Glu-(CO-N-SO2-IQ)-Phe | (SEQ ID NO: 29) | 25 | na |
| 6016: | Arg-Pro-Arg-Thr-Glu-(CO-N-SO2-IQ)-Ser-Phe | (SEQ ID NO: 12) | 1 | 0.1 |
| 6020: | Arg-Pro-Arg-Thr-Ser-Abu-Phe-(O-CO-N-bAla-SO2-IQ) | (SEQ ID NO: 30) | 18 | na |
| 6082: | Arg-Pro-Arg-Thr-Glu-(CO-N-bAla-SO2-IQ)-Ser-Phe | (SEQ ID NO: 31) | 5.54 | 0.2 |
| 6086: | Arg-Pro-Arg-Nle-Glu-(CO-N-bAla-SO2-IQ)-Ser-Phe | (SEQ ID NO: 13) | 0.57 | 0.5 |
| 6088: | Arg-Pro-Arg-Orn-Glu-(CO-N-bGaba-SO2-IQ)-Ser-Phe | (SEQ ID NO: 32) | 1.18 | 1 |
| 6090: | Arg-Pro-Arg-Thr-Glu-(CO-N-Ape5-SO2-IQ)-Ser-Phe | (SEQ ID NO: 33) | 5.6 | 0.6 |
| 6096: | Arg-Pro-Arg-Nle-Glu-(CO-N-bAla-SO2-IQ)-Ser-Nle | (SEQ ID NO: 34) | 0.93 | 0.2 |
| 6102: | Arg-Pro-Arg-Thr-Glu-(CO-N-bAla-S-IQ)-Ser-Phe | (SEQ ID NO: 35) | 0.3 | 0.1 |
| 6104: | Arg-Pro-Arg-Thr-Glu-(CO-N-S-IQ)-Ser-Phe | (SEQ ID NO: 14) | 0.1 | 0.1 |
| 6106: | Arg-Pro-Arg-Thr-Dap-(N-CO-SO2-IQ)-Ser-Phe# | (SEQ ID NO: 38) | 10 | na |
| 6128: | Arg-Pro-Arg-Nle-Glu-(CO-N-SO2-IQ)-Ser-Phe | (SEQ ID NO: 37) | 9 | 0.1 |
| 6130: | Arg-Pro-Arg-Thr-Asp-(CO-N-SO2-IQ)-Ser-Phe | (SEQ ID NO: 38) | 9.5 | 0.053 |
| 6132: | Arg-Pro-Arg-Orn-Glu-(CO-N-SO2-IQ)-Ser-Phe | (SEQ ID NO: 15) | 0.02 | 0.012 |
| 6134: | Arg-Pro-Arg-Nva-Glu-(CO-N-S-IQ)-Ser-Phe | (SEQ ID NO: 39) | 0.217 | 0.018 |
| 6136: | Arg-Pro-Arg-Nle-Glu-(CO-N-S-IQ)-Ser-Phe | (SEQ ID NO: 40) | 0.114 | 0.011 |
| 6138: | Arg-Pro-Arg-Nle-Glu-(CO-N-bAla-SO2-IQ)-Abu-Phe | (SEQ ID NO: 41) | 2 | na |
| 6140: | Arg-Pro-Arg-Nle-Glu-(CO-N-bAla-SO2-IQ)-Dab-Phe | (SEQ ID NO: 42) | 0.413 | 0.195 |
| 6150: | Arg-Pro-Arg-Nva-Glu-(CO-N-SO2-IQ)-Ala-Hol | (SEQ ID NO: 43) | 25 | na |
| 6152: | Arg-Pro-Arg-Nva-Glu-(CO-N-bAla-SO2-IQ)-Ala-Hol | (SEQ ID NO: 44) | 5 | 5 | the small molecule of this compound is connected to the peptide via an amide bond between an amine of Dap residue on the peptide and the carboxylic acid on the small molecule, while in the other compounds the small molecule is connected to the peptide via an amide bond between a carboxylic moiety on the peptide and amino moiety on the small molecule.

na = not assayed

SO2-IQ = 5-aminoethylsulfoneamide isoquinoline

S-IQ = 5-mercaptoaminopropyl isoquinoline

Example 12

Selected Peptides and Peptidomimetic Compounds Serving as Substrate-Mimetic Inhibitors Several peptide and peptidomimetic compounds plates were screened for PKB and PKA inhibition (These results relate to the peptide moiety alone, without the conjugation to a small molecule). Selected results are presented in Table 9.

TABLE 9

| Compound | Sequence | | | | | | % Inhibition | | |
|---|---|---|---|---|---|---|---|---|---|
| | | | | | | | PKB I | PKB II | PKA |
| 60005-5 | Arg | Pro | Arg | Thr | Ser | GlyNH2 | Phe | 96 | 93 | 40 |
| 60005-32 | Arg | Pro | Arg | Thr | GlyNH2 | Ala | Hol | 43 | 44 | 4 |
| 60005-75 | Arg | Pro | Arg | Nval | Ser | GlyNH2 | Hol | 70 | 70 | −4 |
| 60005-84 | Arg | Pro | Arg | Nval | Thr | Ala | Hol | 39 | 48 | 7 |
| 60006-5A | Arg | Pro | Arg | Nval | GlyNH2 | Ala | Hol | 47 | 43 | 10 |
| 60006-7B | Arg | Pro | Arg | Nval | GlyNH2 | Abu | Hol | 53 | 47 | 24 |
| 60006-11B | Arg | Pro | Arg | Nval | GlyNH2 | Dap | Ph2 | 51 | 44 | 20 |
| 60006-16A | Arg | Pro | Arg | Nval | GlyNH2 | GltNH2 | Hol | 42 | 42 | 21 |
| 60006-18A | Arg | Pro | Arg | Nval | Gly | Ala | Hol | 47 | 52 | 11 |
| 60002-38 | Arg | Pro | Arg | Nval | Ser | Ala | Phe | 43 | | −2 |
| 60002-50 | Arg | Pro | Arg | Thr | Ser | Ala | Hol | 62 | | 2 |
| 60002-73 | Arg | Pro | Arg | Thr | Ser | Abu | Hol | 44 | | 8 |
| 60002-88 | Arg | Pro | Arg | Thr | Abu | Dap | Phe | 40 | | −3 |

The most promising peptides from the above described screening were assayed for an accurate $IC_{50}$ curve. In addition, several PTR compounds were designed and based on the screening results, and assayed as well. The results of the $IC_{50}$ evaluation are compiled in Table 10.

TABLE 10

| | Compound | | | | | | | | |
|---|---|---|---|---|---|---|---|---|---|
| IC50 μM | 60002-73 | 60002-38 | 60006-18A | 60006-8A | 60006-5A | 60005-5 | 60018-16 | PTR 6154 | PTR 6158 |
| PKA | 228 | 80 | >100 | 39 | 139 | 7.5 | 100 | >50 | >100 |
| PKB | 34 | 18 | 9.45 | 23 | 10 | 2.4 | 2 | 1.78 | 0.99 |

Figure 3:
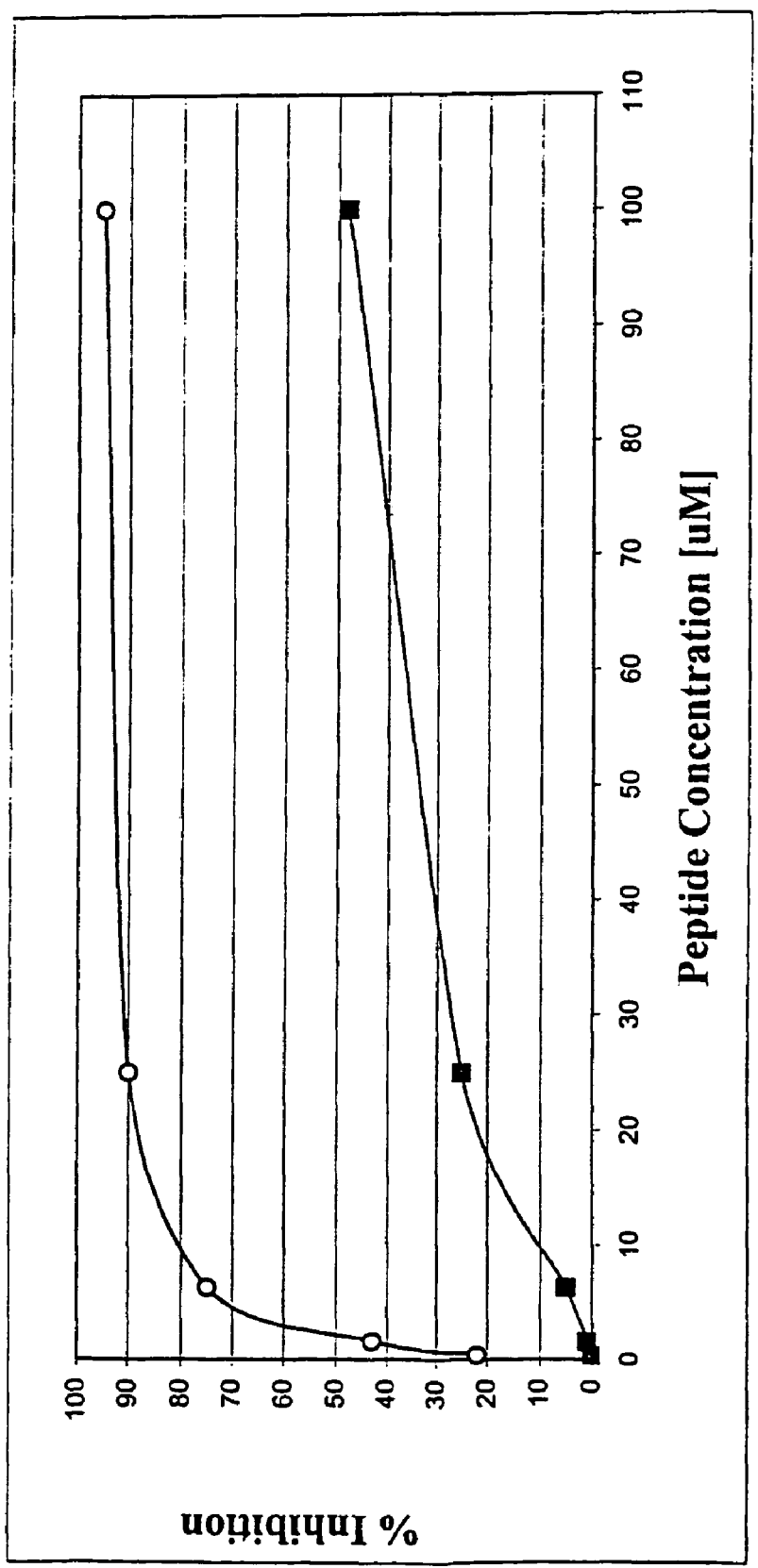
FIG. 3. Describes PKB and PKA inhibition curves ($IC_{50}$) of the active and selective peptide denoted 60018-16.

FIG. 3 describes PKB and PKA inhibition curves ($IC_{50}$) of the active and selective peptide denoted 60018-16.

Based on the best peptide PTR 6158 several analogs were synthesized bearing hydrophobic moieties, as depicted in Table 11. In addition, 5 compounds denoted BP60023 20-24 were synthesized comprising the peptide sequences in Table 11. These are peptides with hydrophobic moieties, aimed for improvement of cell permeability.

Peptides alone showed activity in the order of magnitude of 1 μM, with selectivity PKB/PKA 100X. The peptide alone binds to the substrate site. When conjugated to an ATP moiety, the ATP binds first and the peptide is dislocated, thus the affinity is higher and the selectivity is lower. Synergistic effect on activity. ATP moiety does not distinguish between PKA/PKB sites, thus the ATP domain is not selective

Example 13

Induction of Apoptosis in Prostate Cancer cells

DNA in apoptotic cells is sensitive to denaturation by formamide in contrast to necrotic cells. This sensitivity is due to changes in apoptotic cells chromatin. The specific denaturation was detected with monoclonal antibody to single stranded DNA. Using ssDNA Apoptosis ELISA kit (Chemicon International, Inc.) chimeric compounds were analyzed for their potential to induce apoptosis in PC-3 cells compared to TRAIL (TNF-related apoptosis-inducing ligand), a known apoptotic agent (R&D Systems, Inc.). Results are presented in values of apoptotic index which is calculated by dividing the optical density of treated and untreated cells.

| Compound (50 μM) | Apoptotic index (48 hours) |
|---|---|
| TRAIL | 2.3 |
| 6016 | 3.4 |
| 6082 | 2.6 |
| 6086 | 2.5 |
| 6088 | 1.6 |
| 6096 | 3.2 |
| 6102 | 2.7 |
| 6104 | 2.9 |

TABLE 11

| 20 | Lauryl | Gly | Arg | Pro | Arg | Nva | Tyr | Dap | Hol |
|---|---|---|---|---|---|---|---|---|---|
| 21 | Lauryl | bAla | Arg | Pro | Arg | Nva | Tyr | Dap | Hol |
| 22 | | Myristyl | Arg | Pro | Arg | Nva | Tyr | Dap | Hol |
| 23 | Myristyl | Gly | Arg | Pro | Arg | Nva | Tyr | Dap | Hol |
| 24 | Myristyl | bAla | Arg | Pro | Arg | Nva | Tyr | Dap | Hol |

| Compound (50 μM) | Apoptotic index (48 hours) |
|---|---|
| 6132 | 2.0 |
| 6134 | 2.2 |
| 6136 | 2.4 |
| 6138 | 3.6 |
| 6140 | 4.0 |
| 6152 | 1.5 |
| 6146 | 1.8 |

What is claimed is:

1. A compound of Formula I:

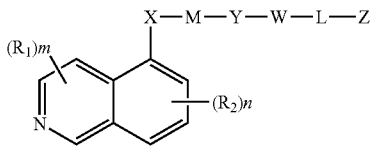

wherein:
R₁ and R₂ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group; m and n are each independently 0-3;
X is selected from the group consisting of SO₂—NH, S and O;
M represents substituted or unsubstituted alkylene of 1-4 carbon atoms;
Y is selected from the group consisting of amide, amine, urea, carbamate, hydrazine or sulfonamide;
Z is Arg-Pro-Arg-R₄-R₅-R₆-R₇;
R₄, R₅, and R₆ are each independently selected from the group consisting of threonine, serine, glutamic acid allyl ester, homocitrulline, lysine, methionine, norleucine, ornithine, arginine, glycine, diaminopropionic acid, diaminobutyric acid, GlyNH₂, and alanine; or are an Nα-ω-functionalized derivative of an amino acid selected from the group of glycine, alanine and tyrosine;
R₇ is selected from the group consisting of phenylalanine, homoleucine, norleucine, glutamic acid allyl ester;
W may be absent so that Y is connected to L or R₄, or W is N-(8-sulfonamide-5-isoquinoline) ethylenediamine; and
L may be absent so that W (if present) or Y is connected to R₄, or L is selected from the group consisting of glycine, β-alanine, phenylalanine, aminobutyric acid and aminopentanoic acid and connects W (if present) or Y with R₄.

2. The compound of claim 1 wherein, in Formula I:
R₁ and R₂ are independently selected from the group consisting of methyl, ethyl, ethoxy and dimethylamine;
m and n are each 1;
M represents substituted or unsubstituted alkylene of 2 carbon atoms; and
Y is selected from the group consisting of amide and amine.

3. The compound according to claim 1 wherein the compound comprises:
Arg-Pro-Arg-Thr-Glu-(bAla-5-mercaptoaminopropyl-isoquinoline)-Ser-Phe (SEQ ID NO: 3).

4. The compound according to claim 1 wherein the compound comprises:
Arg-Pro-Arg-Thr-Glu-(5-mercaptoaminopropyl-isoquinoline)-Ser-Phe (SEQ ID NO: 4).

5. The compound according to claim 1 wherein the compound comprises:
Arg-Pro-Arg-Orn-Glu-(5-aminoethylsulfonamide-isoquinoline)-Ser-Phe (SEQ ID NO: 5).

6. The compound according to claim 1 wherein the compound comprises:
Arg-Pro-Arg-Nva-Glu-(5-mercaptoaminopropyl-isoquinoline)-Ser-Phe (SEQ ID NO: 6).

7. The compound according to claim 1 wherein the compound comprises:
Arg-Pro-Arg-Nle-Glu-(5-mercaptoaminopropyl-isoquinoline)-Ser-Phe (SEQ ID NO: 7).

8. The compound according to claim 1 wherein the compound comprises:
Arg-Pro-Arg-Orn-Glu-(Gly-5-aminoethylsulfonamide)-Dab-Hol (SEQ ID NO: 8).

9. The compound according to claim 1 wherein the compound comprises:
Arg-Pro-Arg-Nle-Glu-(Gly-5-aminoethylsulfonamide)-Dab-Phe (SEQ ID NO: 9).

10. The compound according to claim 1 wherein the compound comprises:
Arg-Pro-Arg-Nle-Glu-(Gly-5-aminoethylsulfonamide)-Dab-Hol (SEQ ID NO: 10).

11. A pharmaceutical composition comprising as an active ingredient a compound according to claim 1, and a pharmaceutically acceptable diluent or carrier.

12. A protein kinase inhibitor comprising as an active ingredient a compound according to claim 1, and a pharmaceutically acceptable diluent or carrier.

13. A method of treatment of diabetes, hemorrhagic shock, or inflammatory disease, comprising administering to a patient in need thereof a therapeutically effective amount of a compound according to claim 1.

14. A compound of Formula I:

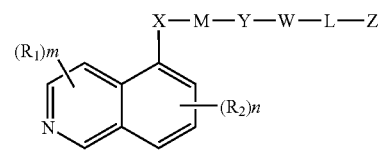

wherein:
R₁ and R₂ are independently selected from the group consisting of hydrogen, a lower alkyl group, a lower alkoxy group, substituted or unsubstituted phenyl group, a lower alkyl substituted with at least one substituent selected from the group consisting of a phenyl group, a halogen, hydroxyl, thiol, nitro, cyano, or amino group; m and n are each independently 0-3;
X is selected from the group consisting of SO₂—NH, S and O;
M represents substituted or unsubstituted alkylene of 1-4 carbon atoms;
Y is selected from the group consisting of amide, amine, area, carbamate, hydrazine or sulfonamide;
W is absent or is selected from the group consisting of substituted or unsubstituted alkylene, aliphatic, aromatic or heterocyclic moiety, of 1-18 carbon atoms;
L is absent or is selected from the group consisting of amide, amine, urea, carbamate, hydrazine or sulfonamide; and
Z is a peptide or peptidomimetic moiety comprising one of the following sequences:
Arg-Pro-Arg-Thr-Glu-Ser-Phe (SEQ ID NO: 3);
Arg-Pro-Arg-Thr-Glu-Ser-Phe (SEQ ID NO 4;
Arg-Pro-Arg-Orn-Glu-Ser-Phe (SEQ ID NO 5);
Arg-Pro-Arg-Nva-Glu-Ser-Phe (SEQ ID NO 6);
Arg-Pro-Arg-Nle-Glu-Ser-Phe (SEQ ID NO 7);

Arg-Pro-Arg-Orn-Glu-Dab-Hol (SEQ ID NO 8);

Arg-Pro-Arg-Nle-Glu-Dab-Phe (SEQ ID NO 9; or

Arg-Pro-Arg-Nle-Glu-Dab-Hol (SEQ ID NO 10); and wherein Y, W if present, or L if present are linked to the Glu residues of the sequences.

15. A pharmaceutical composition comprising as an active ingredient a compound according to claim 14, and a pharmaceutically acceptable diluent or carrier.

16. A protein kinase inhibitor comprising as an active ingredient a compound according to claim 14, and a pharmaceutically acceptable diluent or carrier.

17. A method of treatment of diabetes, hemorrhagic shock, or inflammatory disease, comprising administering to a patient in need thereof a therapeutically effective amount of a compound according to claim 14.

* * * * *

SEQUENCE LISTING

```
<160> NUMBER OF SEQ ID NOS: 44

<210> SEQ ID NO 1
<211> LENGTH: 7
<212> TYPE: PRT
<213> ORGANISM: Artificial
<220> FEATURE:
<223> OTHER INFORMATION: 7-mer motif of PKB substrates
<300> PUBLICATION INFORMATION:
<301> AUTHORS: Dario R. Alessi et al.
<302> TITLE: Molecular Basis for the Substrate Specificity of Protein
      Kinase B; Comparison with MAPKAP Kinase-1 and p70 S6 Kinase
<303> JOURNAL: FEBS Letters
<304> VOLUME: 399
<306> PAGES: 333-338
<307> DATE: 1996-12-16

<400> SEQUENCE: 1

Arg Pro Arg Thr Ser Ser Phe
1               5

<210> SEQ ID NO 2
<211> LENGTH: 6
<212> TYPE: PRT
<213> ORGANISM: Artificial
<220> FEATURE:
<223> OTHER INFORMATION: Consense Sequence of PKB substrates
<220> FEATURE:
<221> NAME/KEY: misc_feature
<222> LOCATION: (2)..(2)
<223> OTHER INFORMATION: Xaa= any amino acid
<220> FEATURE:
<221> NAME/KEY: misc_feature
<222> LOCATION: (4)..(4)
<223> OTHER INFORMATION: Xaa= any amino acid
<220> FEATURE:
<221> NAME/KEY: misc_feature
<222> LOCATION: (5)..(5)
<223> OTHER INFORMATION: Xaa= any amino acid
<220> FEATURE:
<221> NAME/KEY: misc_feature
<222> LOCATION: (6)..(6)
<223> OTHER INFORMATION: Xaa= Ser or Thr
<300> PUBLICATION INFORMATION:
<301> AUTHORS: Toshiyuki Obata et al.
<302> TITLE: Peptide and Protein Library Screening Defines Optimal
      Substrate Motifs for AKT/PKB
<303> JOURNAL: The Journal of Biological Chemistry
<304> VOLUME: 275
<305> ISSUE: 46
<306> PAGES: 36108-36115
<307> DATE: 2000-11-17

<400> SEQUENCE: 2

Arg Xaa Arg Xaa Xaa Xaa
1               5

<210> SEQ ID NO 3
<211> LENGTH: 7
```

```
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=Glu-(bAla-5-mercaptoaminopropyl-
      isoquinoline)

<400> SEQUENCE: 3

Arg Pro Arg Thr Xaa Ser Phe
1               5

<210> SEQ ID NO 4
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=Glu-(5-mercaptoaminopropyl-isoquinoline)

<400> SEQUENCE: 4

Arg Pro Arg Thr Xaa Ser Phe
1               5

<210> SEQ ID NO 5
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Orn
<220> FEATURE:
<221> NAME/KEY: misc_feature
<222> LOCATION: (5)..(5)
<223> OTHER INFORMATION: Xaa=Glu-(5-aminoethylsulfonamide-isoquinoline)

<400> SEQUENCE: 5

Arg Pro Arg Xaa Xaa Ser Phe
1               5

<210> SEQ ID NO 6
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nva
<220> FEATURE:
<221> NAME/KEY: misc_feature
<222> LOCATION: (5)..(5)
<223> OTHER INFORMATION: Xaa=Glu-(5-mercaptoaminopropyl-isoquinoline)

<400> SEQUENCE: 6

Arg Pro Arg Xaa Xaa Ser Phe
1               5

<210> SEQ ID NO 7
<211> LENGTH: 7
<212> TYPE: PRT
<213> ORGANISM: Artificial
```

```
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(5-mercaptoaminopropyl-isoquinoline)

<400> SEQUENCE: 7

Arg Pro Arg Xaa Xaa Ser Phe
1               5

<210> SEQ ID NO 8
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Orn
<220> FEATURE:
<221> NAME/KEY: misc_feature
<222> LOCATION: (5)..(5)
<223> OTHER INFORMATION: Xaa=Glu-(Gly-5-aminoethylsulfonamide)
<220> FEATURE:
<221> NAME/KEY: misc_feature
<222> LOCATION: (6)..(6)
<223> OTHER INFORMATION: Xaa=diaminobutyric acid (Dab)
<220> FEATURE:
<221> NAME/KEY: misc_feature
<222> LOCATION: (7)..(7)
<223> OTHER INFORMATION: Xaa=Homoleucine (Hol)

<400> SEQUENCE: 8

Arg Pro Arg Xaa Xaa Xaa Xaa
1               5

<210> SEQ ID NO 9
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(Gly-5-aminoethylsulfonamide)
<220> FEATURE:
<221> NAME/KEY: misc_feature
<222> LOCATION: (6)..(6)
<223> OTHER INFORMATION: Xaa=diaminobutyric acid (Dab)

<400> SEQUENCE: 9

Arg Pro Arg Xaa Xaa Xaa Phe
1               5

<210> SEQ ID NO 10
<211> LENGTH: 7
<212> TYPE: PRT
<213> ORGANISM: Artificial
<220> FEATURE:
<223> OTHER INFORMATION: syntheic peptide
<220> FEATURE:
<221> NAME/KEY: misc_feature
```

```
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(Gly-5-aminoethylsulfonamide)
<220> FEATURE:
<221> NAME/KEY: misc_feature
<222> LOCATION: (6)..(6)
<223> OTHER INFORMATION: Xaa=diaminobutyric acid (Dab)
<220> FEATURE:
<221> NAME/KEY: misc_feature
<222> LOCATION: (7)..(7)
<223> OTHER INFORMATION: Xaa=homoleucine (Hol)

<400> SEQUENCE: 10

Arg Pro Arg Xaa Xaa Xaa Xaa
1               5

<210> SEQ ID NO 11
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa=biotin-Lys

<400> SEQUENCE: 11

Xaa Gly Arg Pro Arg Thr Ser Ser Phe Ala Glu Gly
1               5                   10

<210> SEQ ID NO 12
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=Glu-(CO-N-5-aminoethylsulfoneamide-
      isoquinoline)

<400> SEQUENCE: 12

Arg Pro Arg Thr Xaa Ser Phe
1               5

<210> SEQ ID NO 13
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(CO-N-bAla-5-aminoethylsulfoneamide-
      isoquinoline)

<400> SEQUENCE: 13

Arg Pro Arg Xaa Xaa Ser Phe
1               5

<210> SEQ ID NO 14
```

```
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=Glu-(CO-N-5-mercaptoaminopropyl-
      isoquinoline)

<400> SEQUENCE: 14

Arg Pro Arg Thr Xaa Ser Phe
1               5

<210> SEQ ID NO 15
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Orn
<220> FEATURE:
<221> NAME/KEY: misc_feature
<222> LOCATION: (5)..(5)
<223> OTHER INFORMATION: Xaa=Glu-(CO-N-5-aminoethylsulfoneamide-
      isoquinoline)

<400> SEQUENCE: 15

Arg Pro Arg Xaa Xaa Ser Phe
1               5

<210> SEQ ID NO 16
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(CO-N-Ala-5-aminoethylsulfoneamide-
      isoquinoline)
<220> FEATURE:
<221> NAME/KEY: misc_feature
<222> LOCATION: (6)..(6)
<223> OTHER INFORMATION: Xaa=diaminobutyric acid (Dab)

<400> SEQUENCE: 16

Arg Pro Arg Xaa Xaa Xaa Phe
1               5

<210> SEQ ID NO 17
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (7)..(7)
<223> OTHER INFORMATION: Xaa=Homoleucine (Hol)

<400> SEQUENCE: 17

Arg Pro Arg Thr Ser Ala Xaa
```

```
                                                           -continued
1               5

<210> SEQ ID NO 18
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa=Abu

<400> SEQUENCE: 18

Arg Pro Arg Val Ser Xaa Phe
1               5

<210> SEQ ID NO 19
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa=Abu
<220> FEATURE:
<221> NAME/KEY: misc_feature
<222> LOCATION: (7)..(7)
<223> OTHER INFORMATION: Xaa=Homoleucine (Hol)

<400> SEQUENCE: 19

Arg Pro Arg Thr Ser Xaa Xaa
1               5

<210> SEQ ID NO 20
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa=Diaminopropionic acid (Dap)
<220> FEATURE:
<221> NAME/KEY: misc_feature
<222> LOCATION: (7)..(7)
<223> OTHER INFORMATION: Xaa=Homoleucine (Hol)

<400> SEQUENCE: 20

Arg Pro Arg Thr Ser Xaa Xaa
1               5

<210> SEQ ID NO 21
<211> LENGTH: 7
<212> TYPE: PRT
<213> ORGANISM: Artificial
<220> FEATURE:
<223> OTHER INFORMATION: synthetic peptide

<400> SEQUENCE: 20

Arg Pro Arg Thr Ser Asp Phe
1               5

<210> SEQ ID NO 22
<211> LENGTH: 7
<212> TYPE: PRT
<213> ORGANISM: Artificial
```

```
<220> FEATURE:
<223> OTHER INFORMATION: synthetic peptide

<400> SEQUENCE: 22

Arg Pro Arg Met Ser Ser Phe
1               5

<210> SEQ ID NO 23
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Orn

<400> SEQUENCE: 23

Arg Pro Arg Xaa Ser Ser Phe
1               5

<210> SEQ ID NO 24
<211> LENGTH: 7
<212> TYPE: PRT
<213> ORGANISM: Artificial
<220> FEATURE:
<223> OTHER INFORMATION: synthetic peptide

<400> SEQUENCE: 24

Arg Pro Arg Arg Ser Ser Phe
1               5

<210> SEQ ID NO 25
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (7)..(7)
<223> OTHER INFORMATION: Xaa=Nle

<400> SEQUENCE: 25

Arg Pro Arg Xaa Ser ser Xaa
1               5

<210> SEQ ID NO 26
<211> LENGTH: 7
<212> TYPE: PRT
<213> ORGANISM: Artificial
<220> FEATURE:
<223> OTHER INFORMATION: synthetic peptide

<400> SEQUENCE: 26

Arg Pro Arg Arg Ser Ser Arg
1               5

<210> SEQ ID NO 27
<211> LENGTH: 7
<212> TYPE: PRT
<213> ORGANISM: Artificial
<220> FEATURE:
<223> OTHER INFORMATION: synthetic peptide
```

```
<220> FEATURE:
<221> NAME/KEY: misc_feature
<222> LOCATION: (4)..(4)
<223> OTHER INFORMATION: Xaa=Orn
<220> FEATURE:
<221> NAME/KEY: misc_feature
<222> LOCATION: (7)..(7)
<223> OTHER INFORMATION: Xaa=Orn

<400> SEQUENCE: 27

Arg Pro Arg Xaa Ser Ala Xaa
1               5

<210> SEQ ID NO 28
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa=Abu
<220> FEATURE:
<221> NAME/KEY: misc_feature
<222> LOCATION: (7)..(7)
<223> OTHER INFORMATION: Xaa=Phe-(O-CO-N-5-aminoethylsulfoneamide-
      isoquinoline)

<400> SEQUENCE: 28

Arg Pro Arg Thr Ser Xaa Xaa
1               5

<210> SEQ ID NO 29
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa=Glu-(CO-N-5-aminoethylsulfoneamide-
      isoquinoline)

<400> SEQUENCE: 29

Arg Pro Arg Thr Ser Xaa Phe
1               5

<210> SEQ ID NO 30
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (6)..(6)
<223> OTHER INFORMATION: Xaa=Abu
<220> FEATURE:
<221> NAME/KEY: misc_feature
<222> LOCATION: (7)..(7)
<223> OTHER INFORMATION: Xaa=Phe-(O-CO-N-bAla-5-aminoethylsulfoneamide-
      isoquinoline)

<400> SEQUENCE: 30

Arg Pro Arg Thr Ser Xaa Xaa
1               5

<210> SEQ ID NO 31
<211> LENGTH: 7
```

```
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=Glu-(CO-N-bAla-5-aminoethylsulfoneamide-
      isoquinoline)

<400> SEQUENCE: 31

Arg Pro Arg Thr Xaa Ser Phe
1               5

<210> SEQ ID NO 32
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Orn
<220> FEATURE:
<221> NAME/KEY: misc_feature
<222> LOCATION: (5)..(5)
<223> OTHER INFORMATION: Xaa=Glu-(CO-N-bGaba-5-aminoethylsulfoneamide-
      isoquinoline)

<400> SEQUENCE: 32

Arg Pro Arg Xaa Xaa Ser Phe
1               5

<210> SEQ ID NO 33
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=Glu-(CO-N-Ape5-5-aminoethylsulfoneamide-
      isoquinoline)

<400> SEQUENCE: 33

Arg Pro Arg Thr Xaa Ser Phe
1               5

<210> SEQ ID NO 34
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(CO-N-bAla-5-aminoethylsulfoneamide-
      isoquinoline)
<220> FEATURE:
<221> NAME/KEY: misc_feature
<222> LOCATION: (7)..(7)
<223> OTHER INFORMATION: Xaa=Nle

<400> SEQUENCE: 34

Arg Pro Arg Xaa Xaa Ser Xaa
```

1               5

<210> SEQ ID NO 35
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=Glu-(CO-N-bAla-5-mercaptoaminopropyl-
      isoquinoline)

<400> SEQUENCE: 35

Arg Pro Arg Thr Xaa Ser Phe
1               5

<210> SEQ ID NO 36
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=diaminopropionic acid (Dap)-(N-CO-5-
      aminoethylsulfoneamide-isoquinoline)

<400> SEQUENCE: 36

Arg Pro Arg Thr Xaa Ser Phe
1               5

<210> SEQ ID NO 37
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(CO-N-5-aminoethylsulfoneamide-
      isoquinoline)

<400> SEQUENCE: 37

Arg Pro Arg Xaa Xaa Ser Phe
1               5

<210> SEQ ID NO 38
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa=Asp-(CO-N-5-aminoethylsulfoneamide-
      isoquinoline)

<400> SEQUENCE: 38

Arg Pro Arg Thr Xaa Ser Phe
1               5

```
<210> SEQ ID NO 39
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nva
<220> FEATURE:
<221> NAME/KEY: misc_feature
<222> LOCATION: (5)..(5)
<223> OTHER INFORMATION: Xaa=Glu-(CO-N-5-mercaptoaminopropyl-
      isoquinoline)

<400> SEQUENCE: 39

Arg Pro Arg Xaa Xaa Ser Phe
1               5

<210> SEQ ID NO 40
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(CO-N-5-mercaptoaminopropyl-
      isoquinoline)

<400> SEQUENCE: 40

Arg Pro Arg Xaa Xaa Ser Phe
1               5

<210> SEQ ID NO 41
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(CO-N-bAla-5-aminoethylsulfoneamide-
      isoquinoline)
<220> FEATURE:
<221> NAME/KEY: misc_feature
<222> LOCATION: (6)..(6)
<223> OTHER INFORMATION: Xaa=Abu

<400> SEQUENCE: 41

Arg Pro Arg Xaa Xaa Xaa Phe
1               5

<210> SEQ ID NO 42
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
```

```
<223> OTHER INFORMATION: Xaa=Nle
<220> FEATURE:
<221> NAME/KEY: misc_feature
<222> LOCATION: (5)..(5)
<223> OTHER INFORMATION: Xaa=Glu-(CO-N-bAla-5-aminoethylsulfoneamide-
      isoquinoline)
<220> FEATURE:
<221> NAME/KEY: misc_feature
<222> LOCATION: (6)..(6)
<223> OTHER INFORMATION: Xaa=diaminobutyric acid (Dab)

<400> SEQUENCE: 42

Arg Pro Arg Xaa Xaa Xaa Phe
1               5

<210> SEQ ID NO 43
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nva
<220> FEATURE:
<221> NAME/KEY: misc_feature
<222> LOCATION: (5)..(5)
<223> OTHER INFORMATION: Xaa=Glu-(CO-N-5-aminoethylsulfoneamide-
      isoquinoline)
<220> FEATURE:
<221> NAME/KEY: misc_feature
<222> LOCATION: (7)..(7)
<223> OTHER INFORMATION: Xaa=Homoleucine (Hol)

<400> SEQUENCE: 43

Arg Pro Arg Xaa Xaa Ala Xaa
1               5

<210> SEQ ID NO 44
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa=Nva
<220> FEATURE:
<221> NAME/KEY: misc_feature
<222> LOCATION: (5)..(5)
<223> OTHER INFORMATION: Xaa=Glu-(CO-N-bAla-5-aminoethylsulfoneamide-
      isoquinoline)
<220> FEATURE:
<221> NAME/KEY: misc_feature
<222> LOCATION: (7)..(7)
<223> OTHER INFORMATION: Xaa=Homoleucine (Hol)

<400> SEQUENCE: 44

Arg Pro Arg Xaa Xaa Ala Xaa
1               5
```